United States Patent [19]

Lentz et al.

[11] Patent Number: 5,360,907
[45] Date of Patent: Nov. 1, 1994

[54] PYRROLO[3,2-B]PYRIDINYLALKYL BENZAMIDE DERIVATIVES

[75] Inventors: Kirk T. Lentz, Niles; Richard M. Weier, Lake Bluff, both of Ill.

[73] Assignee: G.D. Searle & Co., Chicago, Ill.

[21] Appl. No.: 77,598

[22] Filed: Jun. 14, 1993

[51] Int. Cl.$^5$ ................ C07D 471/02; C07D 471/06
[52] U.S. Cl. .................................................. 546/113
[58] Field of Search ....................... 546/113; 514/300

[56] References Cited

U.S. PATENT DOCUMENTS

| | | | |
|---|---|---|---|
| 2,987,518 | 6/1961 | Hoffman et al. | 546/118 |
| 4,003,908 | 1/1977 | Denzel et al. | 546/118 |
| 4,243,671 | 1/1981 | Harris et al. | 514/396 |
| 4,284,641 | 8/1981 | Thorogood | 514/396 |
| 4,357,340 | 11/1982 | Thorogood | 514/396 |
| 4,416,895 | 11/1983 | Thorogood | 514/396 |
| 4,579,862 | 4/1986 | Manley et al. | 514/399 |
| 4,804,658 | 2/1989 | Manley et al. | 514/234.2 |
| 5,019,581 | 5/1991 | Khanna et al. | 514/303 |
| 5,124,335 | 6/1992 | Patchette et al. | 514/300 |
| 5,180,724 | 1/1993 | Bowles | 514/248 |

FOREIGN PATENT DOCUMENTS

| | | |
|---|---|---|
| 0142333 | 5/1985 | European Pat. Off. |
| 0142801 | 5/1985 | European Pat. Off. |
| 2025946 | 1/1980 | United Kingdom |
| WO90/09997 | 9/1990 | WIPO |

OTHER PUBLICATIONS

Goodman and Gilman, *The Pharmacological Basis of Therapeutics*, p. 614 1990.

V. S. Chauhan et al, *Int. J. Peptide Protein Res.*, 15, 96–101 (1980).

W. S. Emerson, *Org. Reactions*, 4, 174 (1948).

J. B. Campbell et al., "Catalysis in Organic Synthesis", pp. 43–47, Academic Press, New York (1980).

*Primary Examiner*—C. Warren Ivy
*Assistant Examiner*—D. Margaret M. Mach
*Attorney, Agent, or Firm*—Scott B. Feder; Roger A. Williams

[57] ABSTRACT

The present invention relates to compounds of the formula

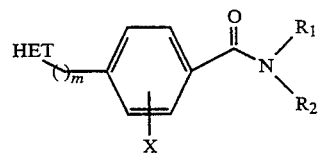

wherein HET is either

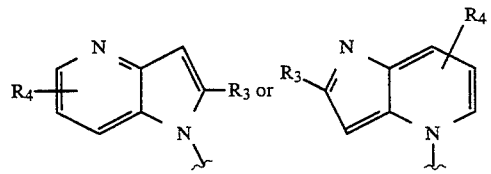

and pharmaceutical compositions containing a therapeutically effective amount of the compounds in combination with a pharmaceutically acceptable carrier and a method for treating diseases mediated by platelet activating factor.

19 Claims, No Drawings

PYRROLO[3,2-B]PYRIDINYLALKYL BENZAMIDE DERIVATIVES

FIELD OF THE INVENTION

This invention relates to pharmaceutical agents (compounds) for treatment of inflammatory and respiratory disorders, such as asthma, vascular disorders, such as cardiovascular and cerebrovascular diseases, and other platelet activating factor mediated diseases, such as septic shock. Of particular interest is a class of novel N,N-cycloalkyl/alkyl benzamides 1H-pyrrolo[3,2-b]pyridine derivatives which class is useful for treatment of disorders mediated by platelet activating factor (PAF).

BACKGROUND OF THE INVENTION

Platelet-activating factor (PAF) has been associated with various biological activities and pathways, thus making it an important mediator responsible for a variety of physiological processes, including activation of platelets, smooth muscle contraction, pathogenesis of immune complex deposition, inflammation, and respiratory, cardiovascular and intravascular alterations. These physiological processes are associated with a large group of diseases, such as cardiovascular disorders, asthma, lung edema, septic shock, adult respiratory distress syndrome and inflammatory diseases.

Various classes of compounds are known for inhibiting platelet activation induced by agents such as arachidonic acid, collagen and platelet activating factor. For example, U.S. Pat. No. 4,804,658 discloses a class of imidazopyridine derivatives useful in the treatment of diseases or disorders mediated by platelet-activating factor. U.S. Pat. No. 2,025,946 to Iizuki, et al. mentions certain classes of imidazoles, which are described as having an inhibitory effect on thromboxane synthetase and as useful for treatment of inflammation, thrombus and asthma. U.S. Pat. Nos. 4,284,641 and 4,416,895 to Thorogood describe certain cycloalkyl/cycloalkenyl imidazoles which inhibit platelet aggregation or reduce the adhesive character of platelets by selective inhibition of thromboxane A2. U.S. Pat. No. 4,537,340 to Thorogood describes a class of 1-arylalkylimidazoles useful for the same purpose. In U.S. Pat. No. 4,243,671 to Harris, et al., the compound 1-(3-phenyl-2-propenyl)1H-imidazole is described as effective in inhibiting thromboxane synthetase, arachidonic acid-induced platelet aggregation and bronchoconstriction.

Compounds are known for use in treating platelet dysfunction or platelet hyperactivity induced specifically by platelet activating factor (PAF). For example, a certain class of glycerol derivatives useful as PAF antagonists is described in EP No. 142,333. A class of indene derivatives is described in EP No. 142,801 as PAF inhibitors. Compounds containing heterocyclic moieties of various types are also known as PAF antagonists. For example, U.S. Pat. No. 4,579,862 to Manley, et al. describes certain imidazole/pyridinylalkanoic acid derivatives as PAF antagonists. U.S. Pat. No. 4,914,108 to Khanna, et al. describes a class of 5-substituted imidazo[4,5-c]pyridine compounds having PAF antagonist activity.

SUMMARY OF THE INVENTION

This invention relates to a novel class of compounds represented by the formula I

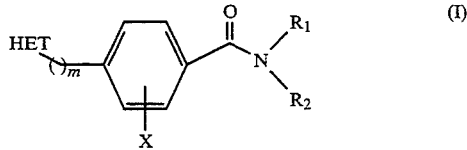

or a pharmaceutically acceptable salt thereof, wherein HET is selected from the group consisting of

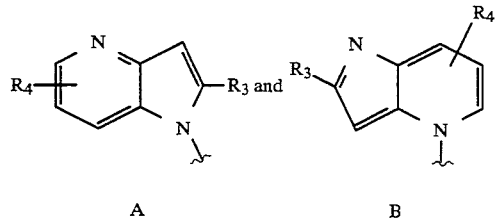

m is an integer from 1 to 4;

$R_1$ and $R_2$ are each independently selected from the group consisting of hydrogen; straight or branched alkyl of 1 to 15 carbon atoms, cycloalkyl having 3 to 8 carbon atoms optionally substituted by one or more alkyl of 1 to 6 carbon atoms, bicycloalkyl having 3 to 8 carbon atoms in each ring, phenyl optionally substituted by one or more groups independently selected from the group consisting of alkyl having 1 to 6 carbon atoms and halogen, straight or branched alkenyl having 3 to 15 carbon atoms, and cycloalkenyl having 3 to 8 carbon atoms;

$R_3$ is selected from hydrogen, alkyl, hydroxyalkyl, formyl, haloalkyl, cycloalkyl, alkylcycloalkyl, cycloalkylalkyl, cycloalkylhaloalkyl, cycloalkylcarbonyl, aralkyl, aralkylhaloalkyl, aryl, haloaryl, aroyl, aryloxyalkyl, alkoxyalkyl, alkylcarbonyl, alkylcarbonylalkyl, alkoxycarbonyl, alkenyl, cycloalkenyl, alkynyl, carboxyl, carboxyalkyl, alkylcarbonyloxyalkyl, alkoxycarbonylalkyl, aralkoxycarbonylalkyl, aralkylcarbonyloxyalkyl, alkylsilyloxyalkyl, aryl/alkylsilyloxyalkyl, arylsilyloxyalkyl, mercaptoalkyl, alkylthioalkyl, alkylsulfinylalkyl, alkylsulfonylalkyl, and may further be an amino or amido radical of the formulae

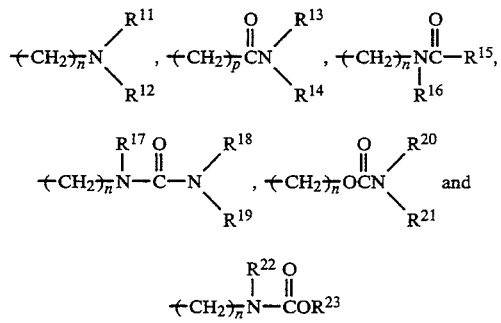

wherein each n is a number independently selected from one to six, inclusive; wherein p is an integer from zero to six; wherein each of $R^{11}$ through $R^{23}$ is independently selected from hydrogen, alkyl, cycloalkyl, hydroxyalkyl, cycloalkylalkyl, alkoxyalkyl, aralkyl and aryl;

X is selected from the group consisting of hydrogen, straight or branched alkyl of 1 to 6 carbon atoms, alkoxy of 1 to 6 carbon atoms, alkoxyalkyl, alkylthio wherein the alkyl has 1 to 6 carbon atoms, hydroxyalkyl wherein the alkyl has 1 to 6 carbon atoms, alkylthioalkyl wherein the alkyl groups each contain 1 to 6 carbon atoms, cyano, hydroxy, amino, alkylamino wherein the alkyl group has 1 to 6 carbon atoms, aminoalkyl, alkylaminoalkyl, dialkylaminoalkyl, dialkylamino wherein the alkyl groups each have 1 to 6 carbon atoms and halogen; and wherein $R_4$ is selected from the group consisting of alkyl of one to six carbon atoms, halogen, alkoxy of one to six carbon atoms and alkylthio.

The present invention also provides pharmaceutical compositions comprised of a therapeutically effective amount of a compound of Formula I in combination with a pharmaceutically acceptable carrier and provides a method for treating diseases mediated by platelet-activating factor.

DETAILED DESCRIPTION OF THE INVENTION

This invention encompasses compounds of the Formula I as previously described.

Within the class of compounds defined by Formula I, there is a subclass of preferred compounds represented by the Formula I wherein $R_1$ and $R_2$ are independently selected from the group consisting of straight or branched chain alkyl of 1 to 6 carbon atoms and cycloalkyl of 3 to 7 carbon atoms.

A more preferred subclass of compounds of the Formula I includes the following compounds:

N-cyclohexyl-N-cyclopentyl-3-methyl-4-(1H-pyrrolo[3,2-b]pyridin-1-ylmethyl)benzamide;
N-cyclopentyl-N-(3,5-dimethylcyclohexyl)-2-methoxy-4-(1H-pyrrolo[3,2-b]pyridin-1-ylmethyl)benzamide;
N-cyclobutyl-N-cyclohexyl-2-methoxy-4-(1H-pyrrolo[3,2-b]pyridin-1-ylmethyl)benzamide;
N-cyclohexyl-3-methoxy-N-(1-methylethyl)-4-(1H-pyrrolo[3,2-b]pyridin-1-ylmethyl)benzamide;
N-cyclohexyl-3-methoxy-N-(1-methylethyl)-4-(4H-pyrrolo[3,2-b]pyridin-4-ylmethyl)benzamide;
3-bromo-N-cyclohexyl-N-(1-methylethyl)-4-(1H-pyrrolo[3,2-b]pyridin-1-ylmethyl)benzamide; and
N-cyclohexyl-2-methoxy-N-(1-methylethyl)-4-(1H-pyrrolo[3,2-b]pyridin-1-ylmethyl)benzamide.

Included within the classes and subclasses of compounds embraced by Formula I are isomeric forms of the described compounds including diastereoisomers, enantiomers and tautomeric forms of the described compounds. Pharmaceutically acceptable salts of such compounds are also included as well as pharmaceutically acceptable salts of such isomers and tautomers.

In the structures herein a bond drawn across a bond in a ring indicates that the bond can be to any available atom of the ring structure.

The term "pharmaceutically acceptable salt," as used herein, refers to conventionally accepted pharmaceutical salts prepared by processes which are well known to those of ordinary skill in the art. [See for example, S. M. Berge, et al., "Pharmaceutical Salts," J. Pharm. Sci., 66:1–19 (1977)].

The term "composition" as used herein means a product which results from the mixing or combining of more than one element or ingredient.

The term "pharmaceutically acceptable carrier" as used herein means a pharmaceutically-acceptable material, composition or vehicle, such as a liquid or solid filler, diluent, excipient, solvent or encapsulating material, involved in carrying or transporting a chemical agent.

The term "therapeutically effective amount" shall mean that amount of drug or pharmaceutical agent that will elicit the biological or medical response of a tissue, system or animal that is being sought by a researcher or clinician.

The term "alkyl" as used herein means a hydrocarbon (linear or branched) radical having from one to twelve carbon atoms, and more preferably from one to six carbon atoms. Representative of such radicals are methyl, ethyl, n-propyl, isopropyl, n-butyl, sec-butyl, isobutyl, tert-butyl, 2-ethylhexyl, n-octyl, 2,4-dimethylpentyl and the like.

The term "halogen" or "halo" as used herein means a fluoro, chloro, bromo or iodo radical.

The term amino denotes a radical of the formula —$NH_2$. The term "alkylamino" as used herein is represented by the radical —$NHR_5$ wherein $R_5$ is an alkyl group as previously described. The term "dialkylamino" as used herein is represented by the radical —$NR_6R_5$ wherein $R_6$ and $R_5$ are the same or different alkyl groups, as defined above. The term "aminoalkyl" as used herein is represented by the formula —$R_9NH_2$ wherein $R_9$ is an alkyl group as defined above. The term "alkylaminoalkyl" is represented by the formula —$R_9NHR_8$ wherein $R_8$ and $R_9$ are the same or different alkyl groups.

The term "haloalkyl" embraces radicals wherein any one or more of the alkyl carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group, such as monofluoromethyl. Dihaloalkyl and polyhaloalkyl groups may be substituted with two or more of the same halo groups, or may have a combination of different halo groups. A dihaloalkyl group, for example, may have two fluorine atoms, such as difluoromethyl and difluorobutyl groups, or two chloro atoms, such as dichloromethyl group, or one fluoro atom and one chloro atom, such as a fluorochloromethyl group. Examples of a polyhaloalkyl are trifluoromethyl, 1,1-difluoroethyl, 2,2,2,-trifluoroethyl, perfluoroethyl, 2,2,3,3-tetrafluoropropyl and perfluoropropyl groups. The term "difluoroalkyl" embraces alkyl groups having two fluorine atoms substituted on any one or two of the alkyl group carbon atoms.

The term "hydroxyalkyl" embraces linear or branched alkyl groups having one to about ten carbon atoms any one or more of which may be substituted with a hydroxyl group.

The term "alkylsilyloxyalkyl" embraces a silyloxyalkylene group wherein such group is attached to the nucleus of Formula I through its alkylene moiety and which group has three terminal alkyl moieties attached to the silyl portion of such group. Similarly, the term "aryl/alkylsilyloxyalkyl" embraces a silyloxyalkylene group wherein such group is attached to the nucleus of Formula I through its alkylene moiety and which group has three terminal moieties selected from alkyl and aryl, which three moieties are attached to the silyl portion of such group. Similarly, the term "arylsilyloxyalkyl"

embraces a silyloxyalkylene group wherein such group is attached to the nucleus of Formula I through its alkylene moiety and which group has three terminal aryl moieties attached to the silyl portion of such group.

The term "alkenyl" embraces linear or branched hydrocarbon radicals having two to about twenty carbon atoms, preferably three to about ten carbon atoms, and containing at least one carbon-carbon double bond, which carbon-carbon double bond may have either cis or trans geometry within the alkenyl moiety, relative to groups substituted on the double-bonded carbons. The term "alkynyl" embraces linear or branched hydrocarbon radicals having two to about twenty carbon atoms, preferably two to about ten carbon atoms, and containing at least one carbon-carbon triple bond.

The term "cycloalkenyl" embraces cyclic radicals having three to about eight ring carbon atoms including one or more double bonds between adjacent ring carbons.

The terms "alkoxy" and "alkoxyalkyl" embrace linear or branched oxy containing radicals each having alkyl portions of one to about ten carbon atoms. An example of an alkoxy is a methoxy group. The term "alkoxyalkyl" further embraces alkyl radicals having two or more alkoxy groups attached to an alkyl radical.

The term "alkylthio" embraces radicals containing a linear or branched alkyl group, of one to about ten carbon atoms attached to a divalent sulfur atom, exemplified by a methylthio group. The terms "sulfinyl" and "sulfonyl", whether used alone or linked to other terms such as "alkyl", denote —SO— and —SO$_2$—, respectively.

The term "aryl" denotes a carbocyclic aromatic ring system composed of one or more aromatic rings. Preferred aryl groups are those consisting of one, two, or three benzene rings. The term "aryl" embraces aromatic radicals such as phenyl, naphthyl and biphenyl. The term "aralkyl" embraces aryl-substituted alkyl radicals such as benzyl, diphenylmethyl, triphenylmethyl, phenylethyl, phenylbutyl and diphenylethyl. The terms "benzyl" and "phenylmethyl" are interchangeable.

The term "amido" denotes a radical consisting of nitrogen atom attached to a carbonyl group, which radical may be further substituted in the manner described herein. The amido radical can be attached to the nucleus of a compound of the invention through the carbonyl moiety or through the nitrogen atom of the amido radical.

The term "cycloalkyl" embraces mono-carbocyclic saturated radicals having three to about eight ring carbon atoms, preferably three to about six carbon atoms, such as cyclopropyl, cyclobutyl, cyclopentyl and cyclohexyl. The term "cycloalkylalkyl" denotes a cycloalkyl radical attached to an alkyl radical which is attachable to a substitutable position of Formula I. Examples of "cycloalkylalkyl" radicals are cyclopentylmethyl and cyclohexylethyl. The term "alkylcycloalkyl" embraces cycloalkyl radicals substituted by an alkyl group as defined above.

The term "cycloalkylhaloalkyl" denotes a cycloalkyl radical attached to a carbon atom of a haloalkyl group as defined above.

The term "formyl" is represented by a radical of the formula —CHO.

The term "cycloalkylcarbonyl" embraces a cycloalkyl radical attached to a "carbonyl" radical of the formula

The term "arylalkylhaloalkyl," as used herein denotes an aralkyl radical as defined above attached via the alkyl portion of the radical to a carbon atom of a haloalkyl radical as defined above.

The term "haloaryl" embraces an aryl radical as defined above substituted on one or more of the ring carbon atoms by the same or different halo radicals as defined above.

The term "aroyl" as used herein denotes an aryl radical as defined above, attached via a ring atom to a carbonyl radical. Representative aroyl radicals include radicals such benzoyl and napthoyl.

The term "bicycloalkyl" as used herein denotes a fused ring system having two fused rings collectively composed of seven to about twelve carbon atoms.

The term "aryloxyalkyl" denotes an aryl radical as defined above attached via a divalent oxygen atom to an alkyl radical as defined above.

The term "alkylcarbonyl" as used herein, denotes an alkyl group as defined above attached to a carbonyl radical as defined above.

The term "alkylcarbonylalkyl" embraces a carbonyl radical as defined above with the same or different alkyl radicals, as defined above, attached to each of its two free valencies.

The term "alkoxycarbonyl" is represented by a radical of the formula —COOR$_7$ wherein R$_7$ is an alkyl group as defined above.

The term "carboxyl" denotes a radical of the formula —COOH.

The term "carboxyalkyl," as used herein, denotes a radical of the formula —R$_7$COOH wherein R$_7$ is an alkyl group as defined above.

The term "alkylcarbonyloxyalkyl" is represented by a radical of the formula R$_8$COOR$_9$— wherein R$_8$ and R$_9$ are the same or different alkyl groups as defined above.

The term "alkoxycarbonylalkyl" is represented by a radical of the formula R$_{24}$OC(O)R$_{25}$— where R$_{24}$ and R$_{25}$ are the same or different alkyl groups as defined above.

The term "aralkoxycarbonylalkyl," as used herein is represented by a radical of the formula R$_{26}$—R$_{27}$—O—C(O)—R$_{28}$— wherein R$_{26}$ is an aryl group as defined above and R$_{27}$ and R$_{28}$ are the same or different alkyl groups as defined above.

The term "aralkylcarbonyloxyalkyl" denotes a radical of the formula R$_{29}$—R$_{30}$—COO—R$_{31}$— wherein R$_{29}$ is an aryl group as defined above and R$_{30}$ and R$_{31}$ are the same or different alkyl groups as defined above.

The term "mercaptoalkyl" as used herein is denoted by a radical of the formula HS—R$_{32}$— wherein R$_{32}$ is an alkyl group as defined above.

The term "alkylthioalkyl" as used herein denotes a radical of the formula R$_{35}$—S—R$_{36}$— wherein R$_{35}$ and R$_{36}$ are the same or different alkyl radicals as defined above.

Compounds of Formula I or their physiologically-acceptable or pharmaceutically-acceptable salts have PAF-antagonistic activity and are of potential value therapeutically as active components in pharmaceutical compositions. Platelet activating factor (PAF) is the phospholipid "1-0-alkyl-2-acetyl-sn-glycero-3-phosphocholine" (AGEPC) which is known as a potent lipid mediator released by animal and human proinflammatory cells. These cells include primarily basophilic and neutrophilic granulocytes, endothelial cells, fibroblasts, epithelial brain cells, macrophages (from blood and tissue) and thrombocytes which are involved in inflammatory reactions.

In pharmacological trials, PAF may cause bronchoconstriction, a lowering of blood pressure, the triggering of thrombocyte aggregation and a proinflammatory activity. Thus PAF is indicated, directly or indirectly, as a mediator in anaphylaxis, in the pathophysiology of allergic conditions, bronchial asthma and in inflammations in general. Compounds of Formula I are therefore suitable for treating patients affected by diseases in which PAF is implicated, including inflammatory or allergic processes or autoimmune diseases. Examples of indications for a PAF antagonist include inflammatory processes of the tracheobronchial tree (acute and chronic bronchitis, bronchial asthma) or of the kidneys (glomerulonephritis), the joints (rheumatic complaints), anaphylactic conditions, allergies and inflammation in the mucous membrances (rhinitis, conjunctivitis) and the skin (e.g. psoriasis, atopic eczema, cold-induced urticaria) and shock caused by sepsis, endotoxins, trauma or burns.

Other important indications for a PAF antagonist include the following: lesions and inflammation in the gastric and intestinal linings, such as shock ulcers, ulcerative colitis, Crohn's disease, ischemic bowel necrosis, stress ulcers and peptic ulcers in general, but particularly ventricular and duodenal ulcers; obstructive lung diseases such as bronchial hyper-reactivity; inflammatory diseases of the pulmonary passages, such as chronic bronchitis; cardio/circulatory diseases such as polytrauma, anaphylaxis and arteriosclerosis; inflammatory intestinal diseases, EPH gestosis (edema-proteinuria hypertension); diseases of extracorporeal circulation, e.g. heart insufficiency, cardiac infarct, organ damage caused by high blood pressure, ischemic diseases, inflammatory and immunological diseases; immune modulation in the transplanting of foreign tissues, e.g. the rejection of kidney, liver and other transplants; immune modulation in leukemia; propagation of metastasis, e.g. in bronchial neoplasia; diseases of the CNS, such as migraine, multiple sclerosis, endogenic depression and agoraphobia (panic disorder). Compounds of Formula I could also be effective as follows: as cyto- and organo-protective agents, e.g. for neuroprotection; to treat DIC (disseminated intravascular coagulation); to treat side effects of drug therapy, e.g. anaphylactoid circulatory reactions; to treat incidents caused by contrast media and other side effects in tumor therapy; to diminish incompatibilities in blood transfusions; to prevent fulminant liver failure ($CCl_4$ intoxication); to treat amanita phalloides intoxication (mushroom poisoning); to treat symptoms of parasitic diseases (e.g. worms); to treat autoimmune diseases (e.g. Werlhof's disease); to treat autoimmune hemolytic anemia, autoimmunologically induced glomerulonephritis, thyroids Hashimoto, primary myxedema, pernicious anemia, autoimmune atrophic gastritis, Addison's disease, juvenile diabetes, Goodpasture syndrome, idiopathic leucopenia, primary biliary cirrhosis, active or chronically aggressive hepatitis (HBsAg-neg.), ulcerative colitis and systemic lupus erythematodes (SLE), ideopathic thrombocytopenic purpura (ITP); to treat diabetes, juvenile diabetes, diabetic retinopathy, polytraumatic shock, haemorrhagic shock; and to treat PAF-associated interaction with tissue hormones (autocoid hormones), lymphokines and other mediators.

The compounds of the present invention can be administered in such oral dosage forms as tablets, capsules, softgels, pills, powders, granules, elixirs or syrups. The compounds can also be administered intravascularly, intraperitoneally, subcutaneously, intramuscularly or topically using forms known to the pharmaceutical art. Moreover, they can be administered rectally, in such forms as suppositories, enemas or bougies. In general the preferred form of administration is oral.

For the orally administered pharmaceutical compositions and methods of the present invention, the foregoing active ingredients will typically be administered in admixture with suitable pharmaceutical diluents, excipients or carriers (collectively referred to hereinafter as "carrier" materials). Such carrier materials are suitably selected with respect to the intended form of administration and consistent with conventional pharmaceutical practices.

For example, for oral administration in the form of tablets or capsules, a therapeutically effective amount of one or more compounds of the present invention can be combined with any oral pharmaceutically acceptable inert carrier such as lactose, starch, sucrose, cellulose, magnesium stearate, calcium sulfate and the like or various combinations thereof. For oral administration in liquid forms, such as in softgels, elixirs, syrups and the like, a therapeutically effective amount of the active drug components can be combined with any oral pharmaceutically acceptable inert carrier such as water, ethanol, polyethylene glycol, vegetable oils, propylene glycol, benzylalcohol and the like or various combinations thereof.

When desired or necessary, suitable binders, lubricants, disintegrating agents, preservatives, and coloring or flavoring agents can also be incorporated into the mixture. Suitable binders include starch, gelatin, natural sugars, corn sweeteners, natural and synthetic gums and waxes and the like, or combinations thereof. Lubricants can include boric acid, sodium benzoate, sodium acetate, sodium chloride and the like, or combinations thereof. Disintegrators include without limitation starch, methylcellulose, agar, bentonite, guar gum and the like, or combinations thereof.

For intravascular, intraperitoneal, subcutaneous or intramuscular administration, one or more compounds of the present invention can be combined with a suitable carrier such as water, saline, aqueous dextrose and the like. For topical administration therapeutically effective amounts of one or more compounds of the present invention can be combined with pharmaceutically acceptable creams, oils, waxes, gels and the like.

Regardless of the route of administration selected, a therapeutically effective amount of the compounds of the present invention are formulated into pharmaceutically acceptable dosage forms by conventional methods known to those skilled in the art. The dosage for preventing or treating PAF mediated conditions with the compounds of the present invention is determined in accordance with a variety of factors, including the type, age, weight, sex and medical condition of patient, the severity of the condition, the route of administration and the particular compound employed in the treatment. A physician or veterinarian of ordinary skill can readily determine and prescribe an effective amount of drug required to prevent or arrest progress of the condition. In so proceeding, the physician or veterinarian could employ relatively low doses at first and subsequently increase the dose until a maximum response is obtained. The daily doses of the compounds of the present invention are ordinarily in the range of about 0.5 mg to about 2000 mg, more preferably in the range of about 350 mg to about 1000 mg.

The compounds of this invention are generally prepared according to reaction schemes I–VII. The benzamides used in the present reactions can be made according to the methodology of WO 89/08653 and U.S. Pat. No. 5,019,581.

group at the para position to give the desired product. A base, such as sodium hydride, is utilized to generate the anion of the 4-azaindole and to direct alkylation to the five-membered ring nitrogen. To synthesize the corresponding 4H compounds (Scheme 1b), the reaction is carried out in the absence of a base.

The syntheses of 4-azaindoles are described in the chemical literature. For example, the syntheses of 5-methoxy-4-azaindole, 2-hydroxymethyl-5-methoxy-4-azaindole and 4-azaindole are described by B. Frydman et al., in the Journal of Organic Chemistry, Volume 33, pp. 3762–3766, in 1968. In addition, a convenient synthesis of 4-azaindole from 2-methyl-3-nitropyridine is described in the Examples Section.

SCHEME I

Scheme 1a

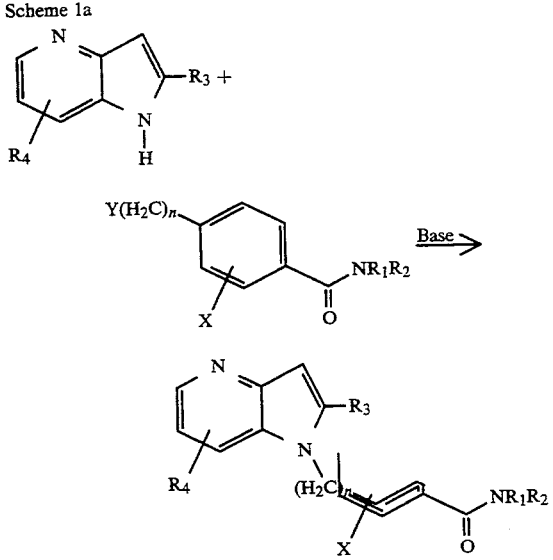

Scheme 1b

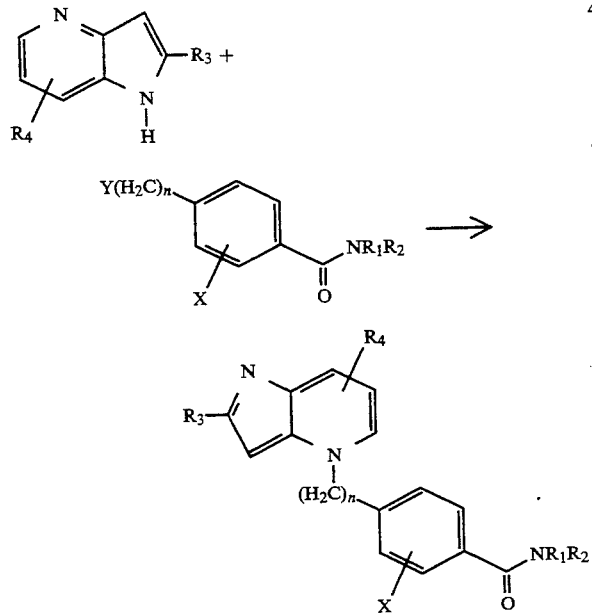

The compounds of the subject invention may be synthesized according to Schemes 1a and 1b above. To synthesize the 1H-4-azaindole compounds (Scheme 1a), the appropriate azaindole is reacted with a suitably substituted benzoic acid amide bearing a haloalkyl

SCHEME II

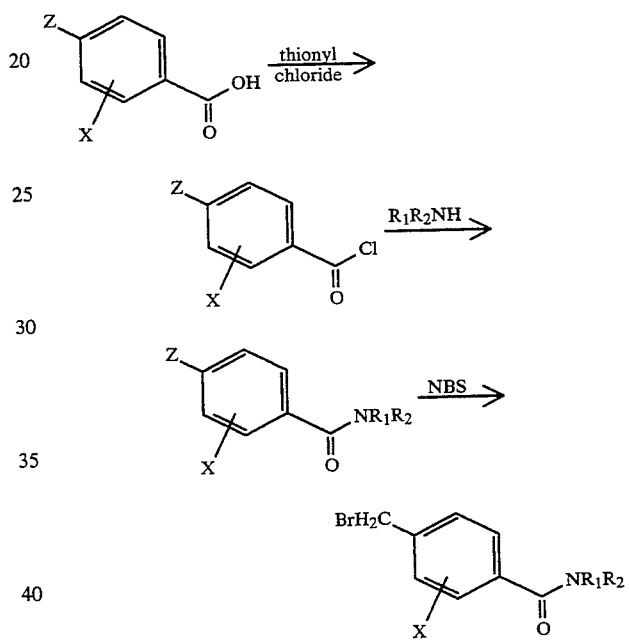

According to Scheme II the acid chlorides are prepared from the corresponding carboxylic acids by treatment with excess thionyl chloride at temperatures of from room temperature to reflux. Excess thionyl chloride is removed by azeotrope with toluene. The residual acid chloride is dissolved in THF and cooled to −10° C. A solution of two molar equivalents of the secondary amine in THF is added dropwise with stirring. When addition is completed, the reaction is allowed to warm to room temperature and stirred for 1–2 hours. The reaction is quenched with 1N HCl, diluted with H₂O and extracted three times with ethyl acetate. The combined organic layers are washed with saturated aqueous sodium bicarbonate solution, with water and with saturated aqueous sodium chloride and dried over sodium sulfate. The drying agent is filtered and the filtrate concentrated in vacuo to give a crude product that is chromatographed on silica gel using mixtures of ethyl acetate and hexane to give the purified amide.

When Z is CH₃, and X is OMe or F, or when Z is H, and X is CH₃, in order to properly place a leaving group on the methyl group, the amide in the scheme above must be treated with a halogenating agent such as N-bromosuccinimide.

For example, a stirred mixture of the purified amide and N-bromosuccinimide (NBS) (1:1 molar ratio) in carbon tetrachloride is irradiated with a sun lamp (150 or 275 W) for 1–3 hours. A white precipitate is filtered and washed with a minimum amount of CHCl₃. The filtrate is washed with water and the aqueous layer, after basification with ammonium hydroxide, is extracted three times with chloroform. All organic layers are combined, washed three times with saturated aqueous sodium chloride solution and dried over sodium sulfate.

The drying agent is filtered and the filtrate concentrated in vacuo to give a crude product that is chromatographed on silica gel using mixtures of ethyl acetate and hexane to give the purified bromomethyl compound.

SCHEME III

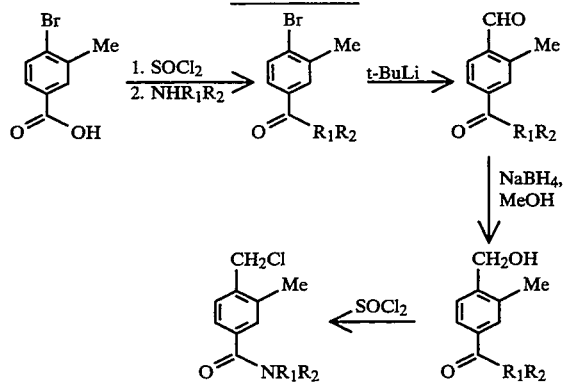

Compounds where X of formula I is substituted with methyl are synthesized from 4-bromo-3-methyl-benzoic acid as shown in Scheme III. The benzoic acid is converted to substituted benzamide by forming the acid chloride and reacting it with the appropriate amine as discussed above. The bromobenzene derivative is treated with an organometallic reagent such as t-butyl lithium and reacted with an electrophile such as dimethylformamide. The resulting aldehyde is reduced to an alcohol with a reducing agent such as sodium borohydride and the hydroxy group converted to a leaving group such as chloro by reacting with thionyl chloride to yield the desired compound.

SCHEME IV

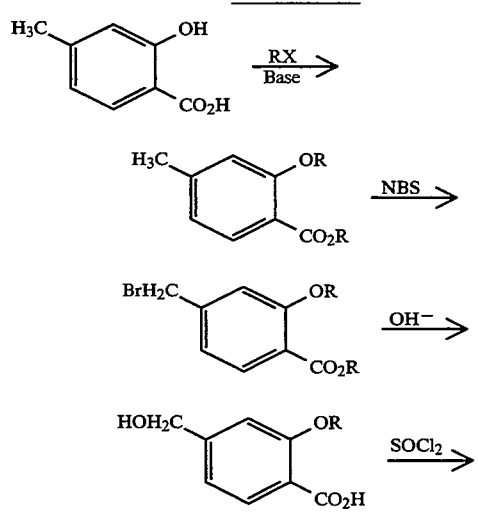

-continued
SCHEME IV

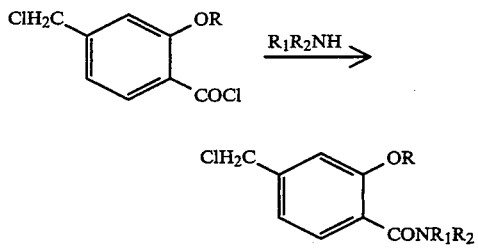

An alternative and preferred method of synthesis of 2-alkoxy-4-halomethylbenzoic acid amides is shown in Scheme IV.

2-Alkoxy-4-chloromethylbenzoic acid amides may be synthesized according to the sequence shown in Scheme IV. The starting 2-hydroxy-4-methyl benzoic acid was converted to the 2-alkoxy ester using an alkyl halide such as methyl iodide in the presence of a base such as potassium carbonate in a solvent such as dimethylformamide at temperatures ranging from room temperature to 60° C. The 2-alkoxy ester is brominated using a free radical brominating agent such as N-bromosuccinimide in the presence of a free radical initiator such as a sun lamp. The resultant 4-bromomethyl carboxylic acid ester is saponified to the acid with concomitant displacement of the benzylic bromide to give the 2-alkoxy-4-hydroxymethyl benzoic acid using a base such as potassium hydroxide in water at temperatures ranging from 80° to ≦100° C. The use of an organic co-solvent is permissible in order to facilitate dissolution of the organic substrate. Suitable co-solvents are dioxane or tetrahydrofuran. The hydroxymethyl derivative is converted to the 4-chloromethyl-2-alkoxybenzoyl chloride derivative by reaction with a chlorinating agent such as thionyl chloride at temperatures ranging from room temperature to 79° C. The acid chloride is then converted to the amide by reaction with the appropriate amine in a solvent such as tetrahydrofuran in the presence of a tertiary amine such as triethylamine to act as a hydrochloric acid scavenger. Temperatures may range from 0° to 60° C.

SCHEME V

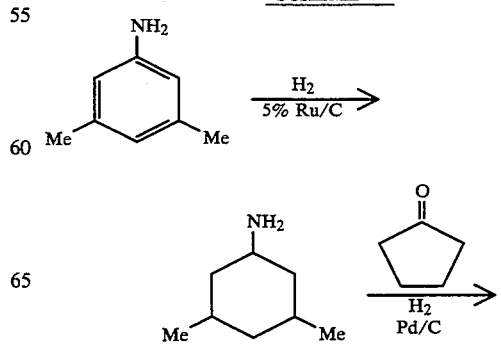

-continued
SCHEME V

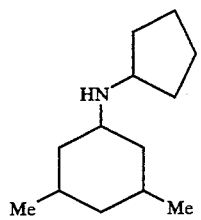

N-cis,cis-3,5-Dimethylcyclohexyl-N-cyclopentyl amine is synthesized as shown in Scheme V. 3,5-Dimethylcyclohexyl amine is synthesized by catalytic hydrogenation of a 3,5-dimethyl aniline for 7 to 24 hours. A suitable catalyst is 5% ruthenium on carbon. Hydrogenation pressure may range from 500 to 1500 psi and temperatures may range from from 80° to 150° C. N-cis,cis-3,5-Dimethylcyclohexyl-N-cyclopentyl amine is formed by reductive amination of cyclopentanone with 3,5-dimethylcyclohexyl amine. The reductive amination may be carried out by hydrogenation using palladium on carbon as a catalyst at pressures ranging from 15 to 90 psi. The temperature may range from room temperature to 50° C. The reaction time is from 7 to 48 hours.

The additional secondary amines may be prepared by any number of methods known to those skilled in the art. See references Emerson, W. S. Org. Reactions 4, 174 1948)

J. B. Campbell, L. B. Lavaginino in "Catalysis in Organic Syntheses" (Jones W. H., ed.) p. 43, Academic Press, New York, 1980.

SCHEME VI

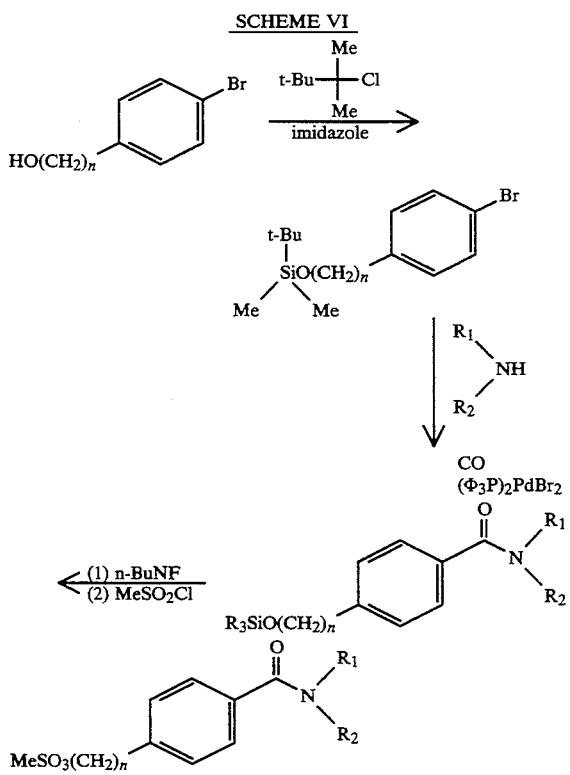

The benzamides used in preparing compounds of Formula I wherein m is 2 or 3 can be prepared according to Scheme VI starting with the appropriate hydroxyalkyl bromobenzene. (This process is described in U.S. Pat. No. 5,019,581). The hydroxyl group is protected as a trialkylsilyl ether by reaction with a trialkylsilyl chloride and imidazole in a suitable solvent such as dimethylformamide. An example of such a protecting group would be the t-butyldimethylsilyl ether. The crude silyl ether is purified by chromatography on silica gel using mixtures of ethyl acetate and hexane. The aryl bromide is converted to the carboxamide according to the procedure of Schoenberg et al. [J. Org. Chem., 39, 3327(1974)]. Thus, the aryl bromide is reacted with carbon monoxide in the secondary amine as solvent using bistriphenylphosphine palladium(II) dibromide as the catalyst at about 100° C. for 8–26 hours in a pressure vessel. The reaction vessel is vented, the reaction mixture triturated with ethyl ether and the washings filtered. The filtrate is washed with 10% aqueous HCl, water and brine. After drying over a suitable drying agent, such as magnesium sulfate, and filtering, the filtrate is concentrated and the residue chromatographed on silica gel using mixtures of ethyl acetate and hexane as eluent to give pure product. The silyl ether is removed by reaction with tetra-n-butylammonium fluoride and the alcohol is converted to a sulfonate ester by reaction with an alkyl or arylsulfonyl chloride. An example of such a sulfonate would be the methanesulfonate.

SCHEME VII
Synthesis of Alkoxyalkyl Benzamides

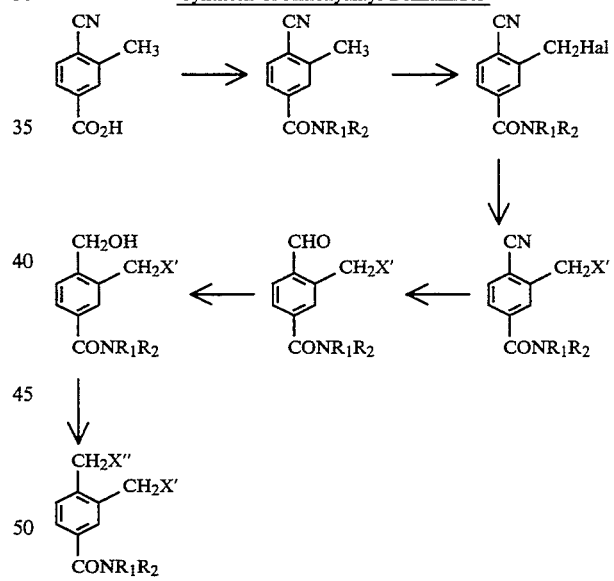

In Scheme VII $R_1$ and $R_2$ are defined as before; "Hal" is halogen; X' is alkoxy, alkylthio and dialkylamino; and X" is chloro, bromo, alkanesulfonyloxy, arylsulfonyloxy or p-toluenesulfonyloxy.

When X of Formula I is substituted with alkoxyalkyl, such substitution may be carried out by methods known to those skilled in the art. Such a method might, for example, employ 4-cyano-3-methyl benzoic acid (F. Fichter, G. Shetty, Helv. Chim. Acta, 20, 563 (1937)) as starting material. This is converted to the appropriate amide by first conversion to the acid chloride by contact with agents such as oxalyl chloride or thionyl chloride and then treating the acid chloride with the desired amine. The amide is converted to the benzylic halide by treatment with a halogenating agent such as N-bromosuccinimide. The halide is versatile and in addition to serving as an intermediate to alkoxyalkyl compounds, is also an intermediate to alkylthioalkyl and alkylaminoalkyl compounds by treatment with the appropriate X' derivative. When halogen is displaced with a metal alkoxide, such as sodium methoxide, the methoxymethyl derivative (X' is OMe) is obtained. Conversion to the aldehyde (X' is OMe) is effected by controlled reduction with a reducing agent such as diisobutylaluminum hydride, followed by acid hydrolysis. Reduction of the aldehyde to the alcohol is effected by a second reduction with another reducing agent such as sodium borohydride or lithium tri-t-butoxyaluminum hydride. The alcohol is converted to a derivative suitable for nucleophilic displacement wherein X" is a leaving group such as halide or aryl or alkyl sulfonate. Such conversion is effected by treatment of the alcohol with, for example, p-toluenesulfonyl chloride, methanesulfonyl chloride, or thionyl chloride.

The following examples illustrate the methods used to prepare the compounds of this invention. These Examples are given by way of illustration only and are not meant to be construed as limiting the invention in spirit or scope as many modifications in materials and methods will be apparent from this disclosure to one having ordinary skill in the art.

STEP A

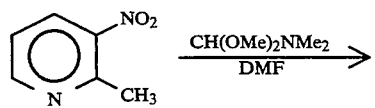

A solution of 2-methyl-3-nitropyridine (4.00 g, 29.0 mmol) [A. Sartorelli et al., *Synthetic Comm.*, 2965–70 (1990)], and dimethyl formamide dimethyl acetal (6.64 ml, 50.0 mmol), in dimethyl formamide (DMF) (40 ml) were refluxed under an argon atmosphere for 2 hours. The resulting red solution was concentrated to yield red crystals (5.48g; 97%). The product was used as is for the next step.

$^1$H NMR (CDCl$_3$, ppm): 3.02 (6H, s); 6.18 (1H, d, J=12.5 Hz); 6.79 (1H, dd, J=10 Hz and 5 Hz); 8.06 (1H, d, J=12.5 Hz); 8.19 (1H, dd, J=10 Hz and 2 Hz); 8.41 (1H, dd, J=5 Hz and 2 Hz).

STEP B

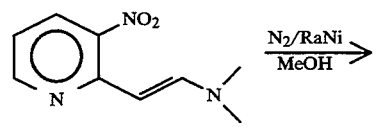

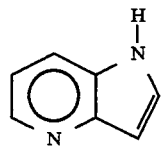

The product from Step A (5.471 g; 28.2 mmol) was hydrogenated at room temperature and atmospheric pressure in methanol for 40 minutes using Raney Nickel (RaNi) as a catalyst. The catalyst was filtered and the filtrate concentrated in vacuo to yield a brown residue (4.4 g). This residue was purified by chromatography on silica gel using CH$_2$Cl$_2$:MeOH:NH$_4$OH(90:10:1) to yield the product (4-azaindole) as an off-white solid (2.04 g; 61%). M.P.=126.0°–127.5° C.

The structural assignment is supported by the proton nmr spectrum.

Anal. Calcd. for C$_7$H$_6$N$_2$: C=71.17, H=5.12, N=23.71; Found: C=70.94, H=5.21, N=23.76.

EXAMPLE 1

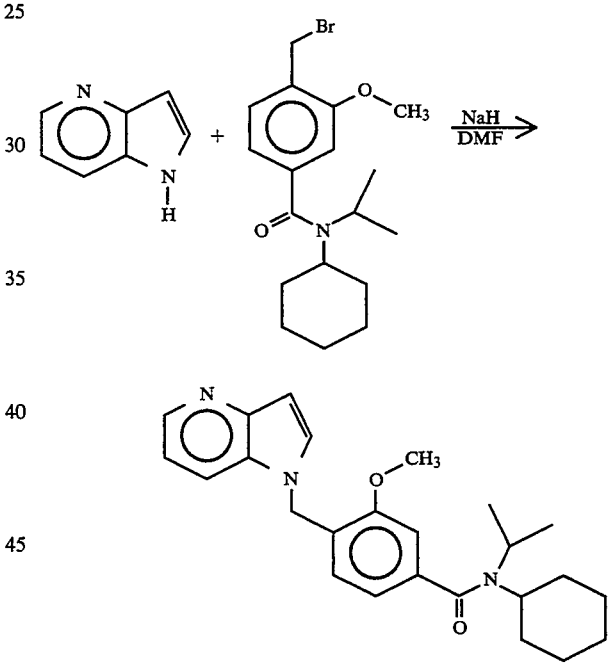

To a stirred solution of 4-azaindole (300 mg; 2.52 mmol) in DMF (15 ml) under an argon atmosphere, was added NaH (110 mg; 2.72 mmol). The reaction mixture was stirred at room temperature for 2 hours. A solution of the benzylic bromide (1.00 g; 2.72 mmol) in DMF (15 ml) was added over a 10 minute period using an addition funnel. The reaction mixture was stirred for 2.5 hours at room temperature and quenched by adding acetic acid (0.25 ml). The solution was filtered through silica gel using CH$_2$Cl$_2$:MeOH:NH$_4$OH (90:10:1). The filtrate was concentrated in vacuo and the brown residue chromatographed twice on silica gel using the same eluent as above. Crystallization from ethyl acetate and hexane yielded tan crystals (618 mg; 60.6%) m.p. 151.5°–152.5° C.

The structural assignment is supported by the nmr spectrum.

Anal. for $C_{25}H_{31}N_3O_2 + 0.25H_2O$: Calcd. C,73.23; H,7.74; N,10.25; Found: C,73.24; H,7.94; N,10.15.

EXAMPLE 2

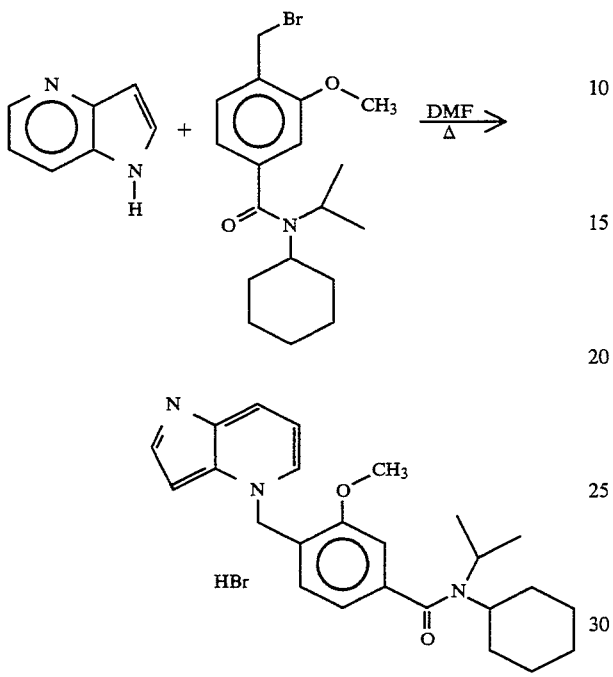

A solution of 4-azaindole (170 mg, 1.44 mmol) and 4-bromomethyl-3-methoxybenzoic acid N,N-isopropyl cyclohexyl amide (640 mg, 1.74 mmol) in DMF (15 ml) was heated to approximately 60° C. and stirred for 1.5 hours. The reaction was cooled and the solvent was concentrated in vacuo to yield a yellow oil that solidified upon trituration with ethyl acetate. The solid was dried under a vacuum and recrystallized from acetonitrile and ethyl acetate to yield a white solid which was the hydrobromide salt of the desired product. M.P. = 196.5°–198.0° C.

The structural assignment is supported by the proton nmr spectrum.

Anal. for $C_{25}H_{31}N_3O_2 + HBr$: Calcd. C,61.70; H,6.84; N,8.64; Br: 16.34; Found: C,61,66; H,6.60; N,8.58; Br:16.66.

The free base was prepared as follows: A solution of the hydrobromide salt (300 mg) in $CH_2Cl_2$, was washed with 10% $K_2CO_3$ and dried ($Na_2SO_4$). The drying agent was filtered and the filtrate concentrated in vacuo to give 250 mg of a yellow oil which crystallized. The collected solid was dried under high vacuum at 100° C. for 7 hours. M.P. = 195.0°–198.0° C.

The structural assignment is supported by the proton nmr spectrum.

Anal. for $C_{25}H_{31}N_3O_2 + 0.5\ H_2O$: Calcd: C,72.20; H,7.76; N,9.91; Found: C,72.43; H,7.78; N,10.14.

EXAMPLE 3

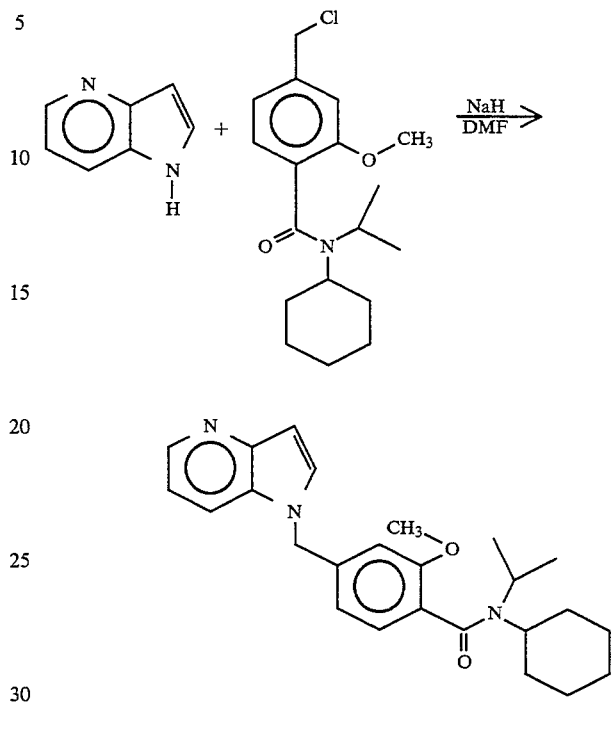

4-Azaindole (300 mg; 2.52 mmol) was added to a stirred suspension of NaH (110 mg, 2.72 mmol) in DMF (10 ml) at room temperature under an argon atmosphere. After stirring for 2 hours a solution of the benzylic chloride (880 mg; 2.72 mmol) in DMF (20 ml) was added dropwise over 10 minutes. The solution was stirred at room temperature for 2 hours and quenched with acetic acid (0.25 ml). The solution was filtered through silica gel and the filter pad was washed thoroughly with $CH_2Cl_2$:MeOH:NH$_4$OH (90:10:1). The filtrate was concentrated in vacuo and the residue taken up in ethyl acetate and water. The aqueous layer was basified with saturated NaHCO$_3$ and extracted three times with ethyl acetate. The organic layers were combined, dried (Na$_2$SO$_4$), and evaporated to yield 1.8 g of crude product. After filtering through silica gel using $CH_2Cl_2$:MeOH:NH$_4$OH (90:10:1) as the eluent followed by concentration in vacuo, the residual brown residue crystallized. Recrystallization from ethyl acetate and hexane, using a trace amount of methanol to complete dissolution, yielded the title compound as a white solid. After drying under high vacuum at 100° C. for 7 hours, there was obtained 676 mg (66%) of desired product, m.p. 178°–181° C.

The structural assignment is supported by the proton nmr spectrum.

Anal. for $C_{25}H_{31}N_3O_2$: Calcd. C,74.04; H,7.70; N,10.36; Found: C,74.05; H,7.68; N,10.26.

EXAMPLE 4

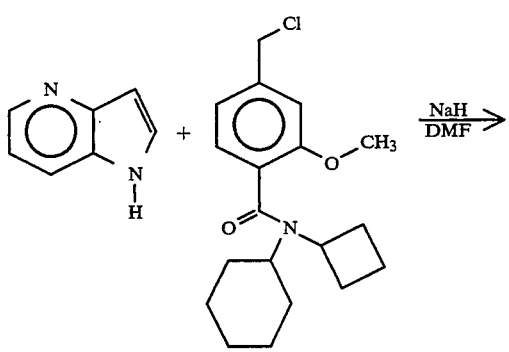

4-Azaindole (300 mg; 2.52 mmol) was added to a stirred suspension of NaH (110 mg; 2.72 mmol) in DMF (1 ml) at room temperature under an argon atmosphere. After stirring for 2 hours, a solution of the benzylic chloride (915 mg; 2.72 mmol) in DMF (15 ml) was added dropwise over 10 minutes. The solution was stirred at room temperature for 2 hours and quenched with acetic acid (0.25 ml). The solution was filtered through silica gel and the filter pad was washed with $CH_2Cl_2$:MeOH:$NH_4OH$ (90:10:1). The filtrate was concentrated in vacuo and the residue taken up in ethyl acetate and water. The aqueous layer was basified with saturated $NaHCO_3$ (15 ml), and extracted with ethyl acetate (5 × 100 ml). The organic layers were combined, dried over $Na_2SO_4$, and evaporated to yield 1.5 g of crude product. After filtering through silica gel using $CH_2Cl_2$:MeOH:$NH_4OH$ (90:10:1) as the eluent, followed by concentration in vacuo, the brown residue crystallized (1.2 g). Recrystallization from ethyl acetate and hexane yielded the title compound as a crystalline solid. The solid was dried under high vacuum at 100° C. for 7 hours to yield 650 mg (62%) of the desired product, m.p. 171°–173° C.

The structural assignment is supported by the proton nmr spectrum.

Anal. for $C_{26}H_{31}N_3O_2$: Calcd. C,74.79; H,7.48; N,10.06; Found: C,74.43; H,7.51; N,9.82.

EXAMPLE 5

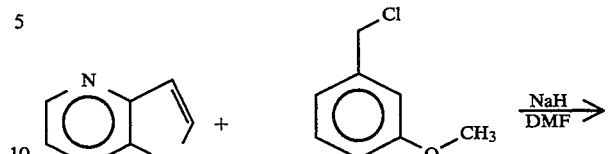

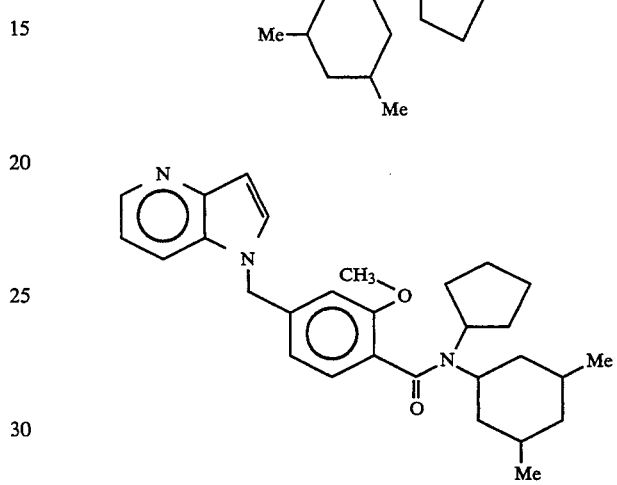

4-Azaindole (280 mg; 2.35 mmol) was added to a stirred suspension of NaH (110 mg; 2.72 mmol) in DMF (15 ml) at room temperature under an argon atmosphere. After stirring for 2 hours a solution of the benzylic chloride (700 mg; 1.85 mmol) in DMF (25 ml) was added dropwise over 10 minutes. The solution was stirred at room temperature for 2 hours and quenched with acetic acid (0.25 ml). The solution was filtered through silica gel using $CH_2Cl_2$:MeOH:$NH_4OH$ (90:10:1). The filtrate was concentrated in vacuo and the residue taken up in ethyl acetate and water. The aqueous layer was basified with saturated $NaHCO_3$ and extracted three times with ethyl acetate. The organic layers were combined, dried over $Na_2SO_4$, and evaporated to yield a yellow-brown residue (1.5 g). The residue was filtered through silica gel using $CH_2Cl_2$:MeOH:$NH_4OH$ (90:10:1) as the eluent and the filtrate concentrated in vacuo to yield a yellow-brown residue. The crude product crystallized from ethyl acetate and hexane to give the title compound as a light yellow solid. After drying under high vacuum at 100° C. for 7 hours 710 mg (83%) of the desired product was obtained, m.p. 177°–178.5° C.

The structural assignment is supported by the proton nmr spectrum.

Anal. for $C_{29}H_{37}N_3O_2$: Calcd. C,75.78; H,8.11; N,9.14; Found: C,75.64; H,8.11; N,9.06.

EXAMPLE 6

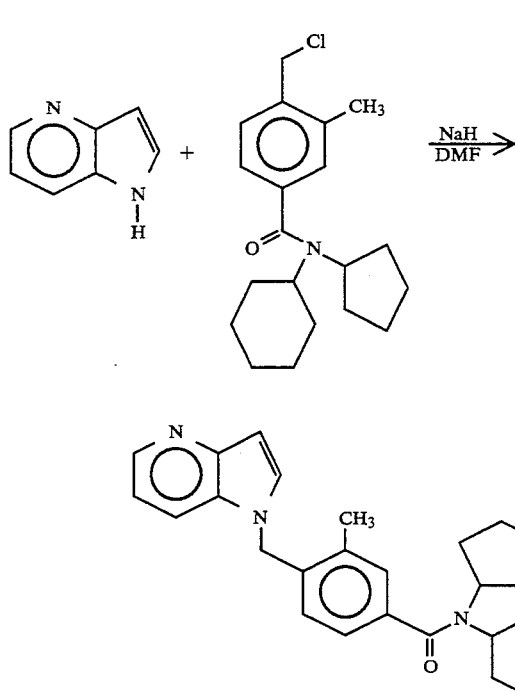

4-Azaindole (300 mg; 2.52 mmol) was added to a stirred suspension of NaH (110 mg; 2.72 mmol) in DMF (15 ml) at room temperature under an argon atmosphere. After stirring for 2 hours a solution of the benzylic chloride (900 mg; 2.72 mmol) in DMF (15 ml) was added dropwise over 10 minutes. The solution was stirred at room temperature for 1.5 hours and quenched with acetic acid (0.25 ml). The solution was concentrated in vacuo using an oil pump to yield a brown solid (2.8 g).

The solid was taken up in ethyl acetate (50 ml) and water. The aqueous layer was basified with saturated NaHCO$_3$ and extracted 3 times with ethyl acetate. The organic layers were combined, dried over Na$_2$SO$_4$ and evaporated to yield crude product. After filtration through silica gel using CH$_2$Cl$_2$:MeOH:NH$_4$OH (90:10:1) as the eluent and concentration of the filtrate in vacuo, 1.07 g of a brown residue was obtained. The solid was crystallized overnight from ethyl acetate and hexane to give the title compound as a white solid. After drying under high vacuum at 100° C. for 7 hours 536 mg (55%) of desired product was obtained. M.P.=181.0°-182.0° C.

The structural assignment is supported by the proton nmr spectrum.

Anal. for C$_{27}$H$_{33}$N$_3$O: Calcd. C,78.04; H,8.00; N,10.11; Found: C,77.87; H,7.99; N,10.00.

EXAMPLE 7

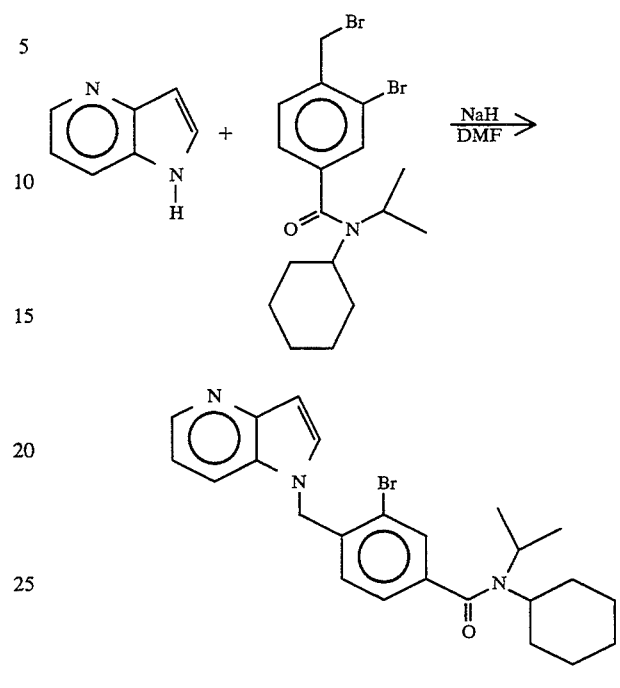

4-Azaindole (300 mg; 2.52 mmol) was added to a stirred suspension of NaH (110 mg; 2.72 mmol) in DMF (15 ml) at room temperature under an argon atmosphere. After stirring for 2 hours, a solution of the benzylic bromide (1.5 g; 2.73 mmol) in DMF (15 ml) was added dropwise over 10 minutes. The solution was stirred at room temperature for 1.5 hours and quenched with acetic acid (0.25 ml). The solution was concentrated in vacuo using an oil pump to yield a brown oil (3.8 g).

The oil was taken up in ethyl acetate (50 ml), washed three times with 10% NaHCO$_3$, dried over MgSO$_4$, filtered through silica gel and evaporated to yield a brown oil. The oil was passed through silica gel using ethyl acetate:hexane:triethylamine (90:10:2) as the eluent. Concentration of the combined fractions in vacuo yielded an orange-brown residue (1.0 g). The residue was crystallized overnight from ethyl acetate and hexane to give the title compound as a crystalline solid. After drying under high vacuum at 100° C. for 7 hours 484 mg (45%) of the desired product was obtained, (m.p. 148°-149° C.).

The structural assignment is supported by the proton nmr spectrum.

Anal. for C$_{24}$H$_{28}$N$_3$OBr: Calcd. C,63.44; H,6.21; N,9.25; Br,17.58; Found: C,63.31; H,6.25; N,9.17; Br,17.28.

EXAMPLE 8

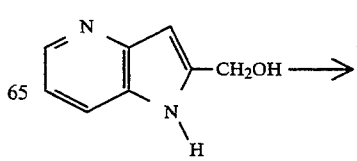

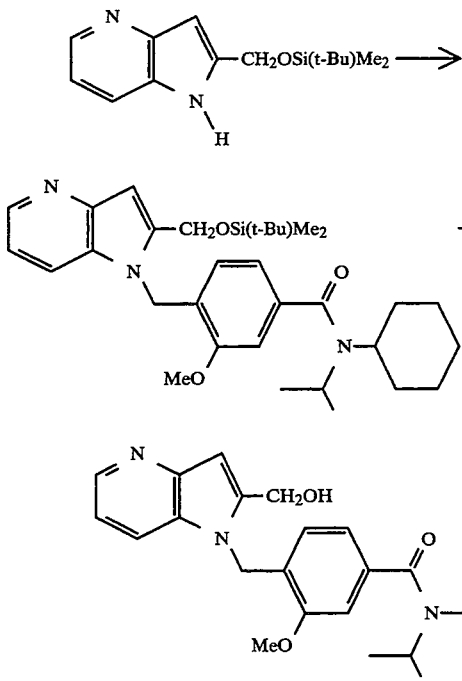

A solution of 2-hydroxymethyl-4-azaindole [B. Frydman et al., *J. Org. Chem.*, 33, 3762 (1968)] (993 mg, 6.7 mmol), tert.-butyldimethylsilyl chloride (1.1 g, 7.3 mmol) and imidazole (460 mg, 6.76 mmol) in dimethylformamide (10 ml) is stirred for 3 hours at room temperature under an argon atmosphere. The reaction solvent is removed in vacuo using an oil pump. The residue is taken up in ethyl acetate, washed twice with 5% NaHCO₃, once with saturated NaCl solution and dried (Na₂SO₄). The drying agent is filtered and the filtrate is concentrated in vacuo to give the product. Purification is effected by chromatography on silica gel using mixtures of ethyl acetate, hexane and triethylamine as eluents.

The 4-azaindole (661 mg, 2.52 mmol) from the above experiment is added to a stirred suspension of NaH (110 mg, 2.72 mmol) in DMF (15 ml) at room temperature under an argon atmosphere. After stirring for 2 hours, a solution of the benzylic bromide (1.0 g, 2.72 mmol) in DMF (15 ml) is added dropwise over 10 minutes. The reaction mixture is stirred at room temperature for 1.5 hours and quenched with acetic acid (0.25 ml). The reaction is concentrated in vacuo using the oil pump to yield a brown oil. The residue is taken up in ethyl acetate, washed three times with 10% NaHCO₃, and dried (MgSO₄). The drying agent is filtered and the filtrate is concentrated in vacuo to give the crude product. The desired pure compound is obtained by chromatography on silica gel using mixtures of methylene chloride, methanol and ammonium hydroxide as eluents. Alternative eluents are mixtures of ethyl acetate, hexane and triethylamine or of ethyl acetate, methanol and ammonium hydroxide.

A solution of the silyl ether from above (730 mg, 1.8 mmol) in tetrahydrofuran (10 ml) is treated with a solution of tetra-n-butyl ammonium fluoride (3.6 ml of a 1M solution in THF) with stirring for 3 hours at room temperature. The reaction mixture is poured onto 15 ml of saturated aqueous NaHCO₃ solution and extracted twice with CH₂Cl₂. The combined organic layers are dried (Na₂SO₄), filtered and the filtrate concentrated in vacuo to give the crude product. Purification is effected by chromatography on silica gel using mixtures of ethyl acetate, methanol and ammonium hydroxide.

EXAMPLE 9

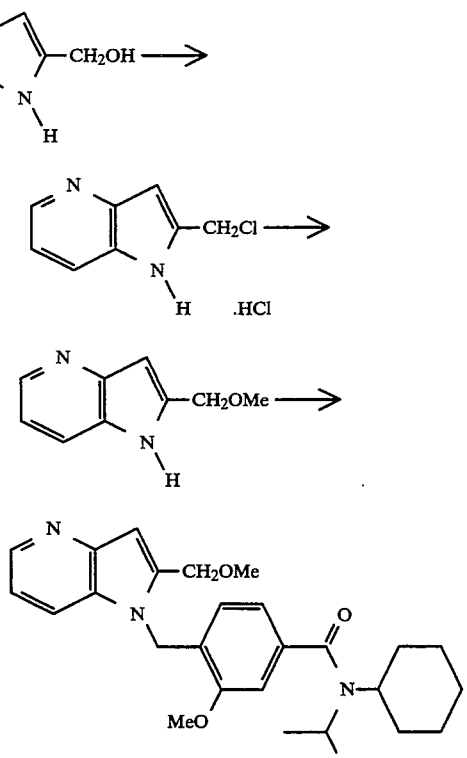

2-Chloromethyl-4-azaindole, isolated as the monohydrochloride salt, is synthesized from 2-hydroxymethyl-4-azaindole by a procedure analogous to that described for the synthesis of 2-chloromethyl-1H-imidazo[4,5-b]pyridine monohydrochloride in the J. Het. Chem., 2, 759-760 (1969).

Crude 2-chloromethyl-4-azaindole monohydrochloride (3.0 g, approximately 14.8 mmol) is added to a 25% solution of sodium methoxide in methanol (16.8 ml) and the reaction is refluxed with stirring for 8 hours under an argon atmosphere. The reaction is concentrated and the residue is chromatographed on silica gel using mixtures of CH₂Cl₂, MeOH, and NH₄OH as eluents to give pure 2-methoxymethyl-4-azaindole.

2-Methoxymethyl-4-azaindole (1.62 g, 10 mmol) is added to a stirred slurry of washed NaH (from 400 mg of a 60% dispersion in silicone oil; 10 mmol) in DMF (20 ml) at 0° C. under an argon atmosphere. After warming to room temperature, the reaction is stirred for 2 hours, cooled again to 0° C. and 3-methoxy-4-bromomethyl N,N-isopropyl cyclohexyl benzamide (3.68 g, 10.0 mmol) is added. The reaction is stirred at room temperature overnight, quenched with aectic acid, and concentrated in vacuo using an oil pump. The residue is dissolved in EtOAc, washed with aqueous NaHCO₃, water and dried (Na₂SO₄). The drying agent is filtered and the filtrate is concentrated in vacuo to give the crude product. Purification is effected by chromatography on silica gel using mixtures of CH₂Cl₂, MeOH, and NH₄OH as eluents to give the desired purified compound.

EXAMPLE 10

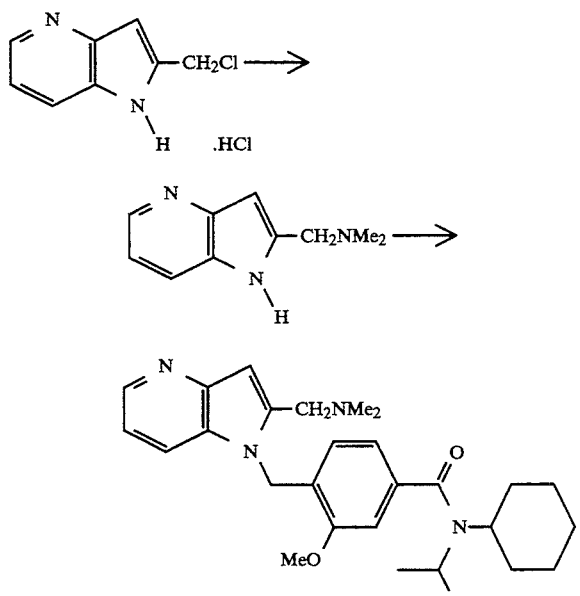

2-Dimethylaminomethyl-4-azaindole is synthesized from 2-hydroxymethyl-4-azaindole by a procedure analogous to that described for the synthesis of 2-dimethylaminomethyl-1H-imidazo[4,5-b]pyridine monohydrochloride in the J. Het. Chem., 6, 759–760 (1969).

2-Dimethylaminomethyl-4-azaindole (1.75 g, 10 mmol) is added to a stirred slurry of washed NaH (from 400 mg of a 60% dispersion in silicone oil; 10 mmol) in DMF (20 ml) at 0° C. under an argon atmosphere. After warming to room temperature, the reaction is stirred for 2 hours, cooled again to 0° C. and 3-methoxy-4-bromomethyl N,N-isopropyl cyclohexyl benzamide (3.68 g, 10.0 mmol) is added. The reaction is stirred at room temperature overnight, quenched with AcOH, and concentrated in vacuo using an oil pump. The residue is dissolved in EtOAc, washed with aqueous NaHCO3, water and dried (Na2SO4). The drying agent is filtered and the filtrate is concentrated in vacuo to give the crude product. Purification is effected by chromatography on silica gel using mixtures of CH2Cl2, MeOH, and NH4OH as eluents to give the desired purified compound.

EXAMPLE 11

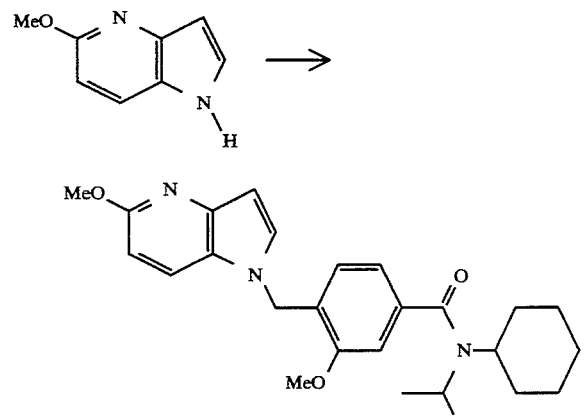

5-Methoxy-4-azaindole [B. Frydman et al., J. Org. Chem., 33, 3762 (1968)] (1.48 g, 10 mmol) is added to a stirred slurry of washed NaH (from 400 mg of a 60% dispersion in silicone oil; 10 mmol) in DMF (20 ml) at 0° C. under an argon atmosphere. After warming to room temperature, the reaction is stirred for 2 hours, cooled again to 0° C. and 3-methoxy-4-bromomethyl N,N-isopropyl cyclohexyl benzamide (3.68 g, 10.0 mmol) is added. The reaction is stirred at room temperature overnight, quenched with AcOH, and concentrated in vacuo using an oil pump. The residue is dissolved in EtOAc, washed with aqueous NaHCO3, water and dried (Na2SO4). The drying agent is filtered and the filtrate is concentrated in vacuo to give the crude product. Purification is effected by chromatography on silica gel using mixtures of CH2Cl2, MeOH, and NH4OH as eluents to give the desired purified compound.

EXAMPLE 12

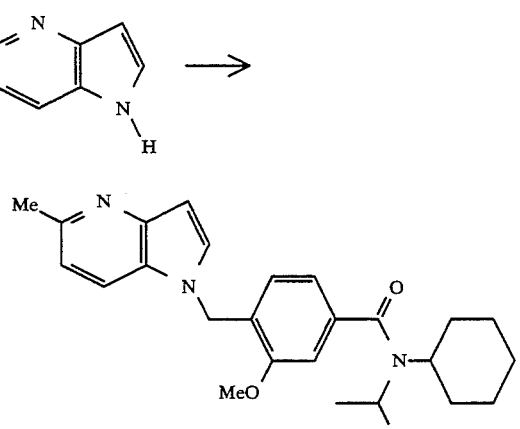

5-Methyl-4-azaindole [J. E. Macor, U.S. Pat. No. 5,051,412, Sep. 24, 1991] (1.32 g, 10 mmol) is added to a stirred slurry of washed NaH (from 400 mg of a 60% dispersion in silicone oil; 10 mmol) in DMF (20 ml) at 0° under an argon atmosphere. After warming to room temperature, the reaction is stirred for 2 hours, cooled again to 0° and 3-methoxy-4-bromomethyl N,N-isopropyl cyclohexyl benzamide (3.68 g, 10.0 mmol) is added. The reaction is stirred at room temperature overnight, quenched with acetic acid, and concentrated in vacuo using an oil pump. The residue is dissolved in EtOAc, washed with aqueous NaHCO3, water and dried (Na2SO4). The drying agent is filtered and the filtrate is concentrated in vacuo to give the crude product. Purification is effected by chromatography on silica gel using mixtures of CH2Cl2, MeOH, and NH4OH as eluents to give the purified compound.

EXAMPLE 13

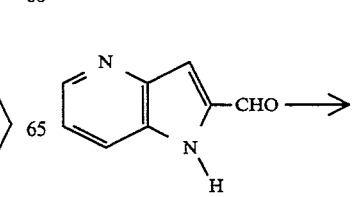

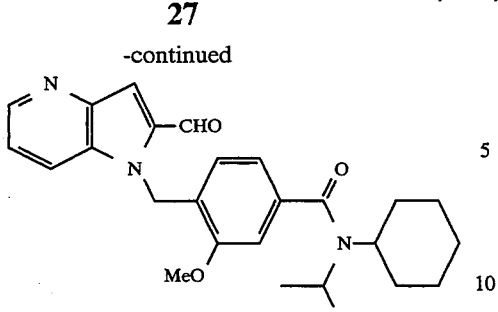

2-Formyl-4-azaindole [B. Frydman et al., J. Org. Chem., 33, 3762 (1968)] (1.46 g, 10 mmol) is added to a stirred slurry of washed NaH (from 400 mg of a 60% dispersion in silicone oil; 10 mmol) in DMF (20 ml) at 0° under an argon atmosphere. After warming to room temperature, the reaction is stirred for 2 hours, cooled again to 0° and 3-methoxy-4-bromomethyl N,N-isopropyl cyclohexyl benzamide (3.68 g, 10.0 mmol) is added. The reaction is stirred at room temperature overnight, quenched with acetic acid, and concentrated in vacuo using an oil pump. The residue is dissolved in EtOAc, washed with aqueous $NaHCO_3$, water and dried ($Na_2SO_4$). The drying agent is filtered and the filtrate is concentrated in vacuo to give the crude product. Purification is effected by chromatography on silica gel using mixtures of $CH_2Cl_2$, MeOH, and $NH_4OH$ as eluents to give the purified compound.

EXAMPLE 14

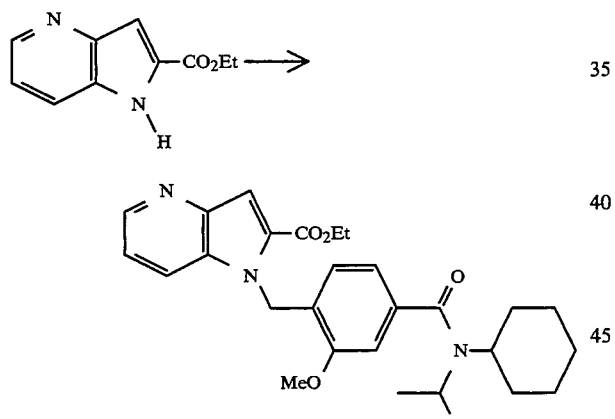

Ethyl 4-azaindole-2-carboxylate [B. Frydman et al., J. Org. Chem., 33, 3762 (1968)] (1.90 g, 10 mmol) is added to a stirred slurry of washed NaH (from 400 mg of a 60% dispersion in silicone oil; 10 mmol) in DMF (20 ml) at 0° under an argon atmosphere. After warming to room temperature, the reaction is stirred for 1 hour cooled again to 0° and 3-methoxy-4-bromomethyl N,N-isopropyl cyclohexyl benzamide (3.68 g, 10.0 mmol) is added. The reaction is stirred at room temperature overnight, quenched with acetic acid, and concentrated in vacuo using an oil pump. The residue is dissolved in EtOAc, washed with aqueous $NaHCO_3$, water and dried ($Na_2SO_4$). The drying agent is filtered and the filtrate is concentrated in vacuo to give the crude product. Purification is effected by chromatography on silica gel using mixtures of $CH_2Cl_2$, MeOH, and $NH_4OH$ as eluents to give the purified compound. Alternatively, mixtures of ethyl acetate, hexane and triethylamine may be used as eluents.

EXAMPLE 15

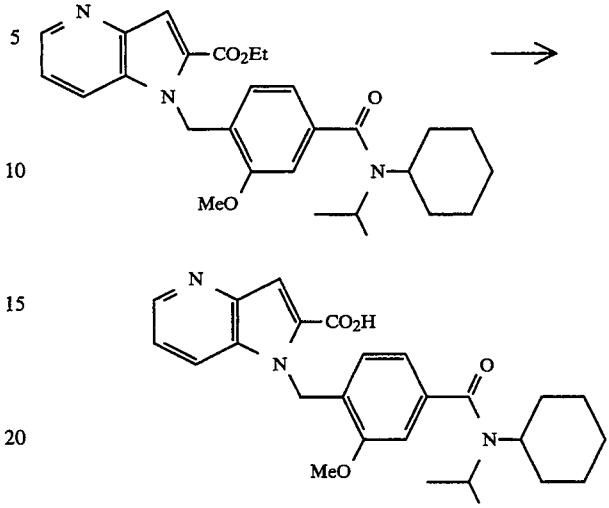

The ethyl ester obtained above (4.78 g) is treated with 2N potassium hydroxide solution (100 ml) at reflux with stirring until saponification is complete as evidenced by thin layer chromatography data. The reaction solution is cooled and adjusted to pH 4 using glacial acetic acid. After cooling at 5° C. for several hours, the crystalline deposit is filtered to give the desired compound. Alternatively, the acidified reaction mixture is extracted thoroughly with $CH_2Cl_2$. The combined organic layers are dried ($Na_2SO_4$), the drying agent filtered and the filtrate concentrated in vacuo.

EXAMPLE 16

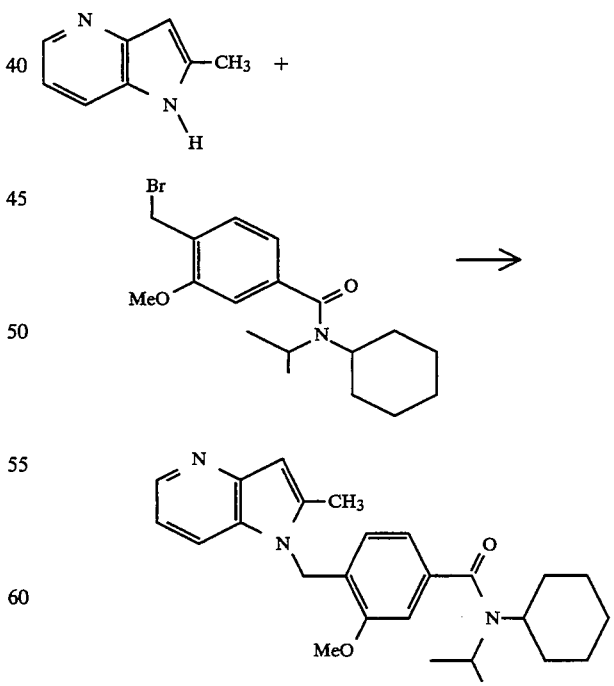

2-Methyl-4-azaindole [G. R. Clemo and G. A. Swan, J. Chem. Soc., 198 (1948)] (1.32 g, 10 mmol) is added to a stirred slurry of washed NaH (from 400 mg of a 60% dispersion in silicone oil; 10 mmol) in DMF (20 ml) at 0°

C. under an argon atmosphere. After warming to room temperature, the reaction is stirred for 2 hours, cooled again to 0° and 3-methoxy-4-bromomethyl N,N-isopropyl cyclohexyl benzamide (3.68 g, 10.0 mmol) is added. The reaction is stirred at room temperature overnight, quenched with AcOH, and concentrated in vacuo using an oil pump. The residue is dissolved in EtOAc, washed with aqueous $NaHCO_3$, water and dried ($Na_2SO_4$). The drying agent is filtered and the filtrate is concentrated in vacuo to give the crude product. Purification is effected by chromatography on silica gel using mixtures of $CH_2Cl_2$, MeOH, and $NH_4OH$ as eluents to give the purified title compound.

BIOLOGICAL EVALUATION

Assay A: Human Platelet Receptor Binding

Compounds of the invention were evaluated for their ability to inhibit specific binding of [$^3$H]PAF to human platelet membrane preparation. Human packed platelets were obtained from Lifesource, Inc. (Glenview, Ill.) and washed 3 times with 10 mM Trizma pH 7.0, 2 mM EDTA (dipotassium salt), 150 mM KCl and then once with 10 mM Trizma 7.4, 20 mM $CaCl_2$. The platelets were broken by freezing in a dry ice-ethanol bath, followed by thawing in 24° C. water baths. The preparation was centrifuged (40,000×g, 20 minutes, 4'C) and the pellet suspended in 10 mM Trizma 7.4, 20 mM $CaCl_2$, 5 mg/ml human albumin. Protein concentration in the platelet membrane preparation was determined by the Lowry method [O. H. Lowry et al., J. Biol. Chem., 193, 265–275 (1951)]. Aliquots of the membrane preparation were stored at $-70°$ C. Each preparation was characterized for PAF receptor number and dissociation constant (Kd). In binding assays 5 μl of test compound, solubilized in DMSO, was added to polypropylene tubes along with 0.75 nM [$^3$H]PAF and 200 mcl [0.075 nM] of membranes and 95 μl 10 mM Trizma 7.4, 20 mM $CaCl_2$, 5 mg/ml human albumin. Tubes were incubated for 30 minutes at 24° C. The incubation was terminated by adding 4 ml of ice-cold 10 mM Trizma pH 7.4, 20 mM $CaCl_2$ and 20 mg/ml BSA prior to vacuum filtration using Whatman GF/C filters. Filters were prepared and counted for a scintillation counter. All DPM values were corrected for background and isotope decay. Triplicate determinations for single doses were averaged. The amount of non-specific binding was subtracted from all dose averages, giving an amount of specific binding in all cases. The $IC_{50}$ values for the compounds of the invention were determined by the Allfit program using percent displacement data. (Allfit is a 'basic' computer program for simultaneous curve fitting of a family of signoidal dose-response curves using the four parameter logistic equation.) Results are shown in Table I.

Assay B: Human Platelet Aggregation Inhibition

Compounds of the invention were evaluated for their ability to inhibit PAF-induced aggregation of human platelets in a human-platelet-rich plasma. Venous blood was collected from donors who fasted for 8 hours and were instructed not to use antiinflammatory drugs for 2 weeks prior to the blood draw. Blood was collected into syringes containing 0.1 ml of 3.8% [w/v] citrate and centrifuged in polypropylene tubes at 150 xg for 20 minutes at room temperature. The platelet rich plasma [PRP] was collected and let sit for 20 minutes at room temperature. Platelet activating factor [PAF] was diluted in 0.9% NaCl with 0.25% bovine serum albumin.

Silicon treated cuvettes with stir bars were placed in the 37° heating block of the platelet aggregometer [Bio-Data Corporation, Platelet Aggregation Profiler, Model PAP-4]. PRP and test compound were added to cuvettes and aggregation monitored for 10–15 seconds at 37° with stirring. PAF was added and aggregation monitored for an additional 3 minutes. Peak aggregation was considered the peak of the first aggregation wave, usually 45–60 seconds after PAF addition. Inhibition of aggregation was determined by the following: $1 - [(\%\text{ aggregation in the presence of compound}) \div (\%\text{ maximal aggregation})]$. A log/logit transformation was used to determine half maximal inhibitory concentration of a test compound [$IC_{50}$]. Results are shown in Table I.

TABLE I

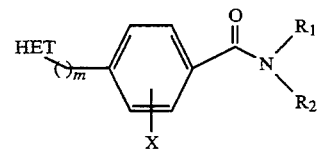

| Example | X | $R_1$ | $R_2$ | Human Platelet Receptor $IC_{50}$ (nM) | Human Platelet Aggregation $IC_{50}$ (nM) |
|---|---|---|---|---|---|
| 7 | 2-Br | i-Pr | c-Hex | 8 | |
| 6 | 2-Me | c-Pent | c-Hex | 39 | |
| 5 | 3-OMe | c-Pent | 3,5-di-Me-c-Hex | 15 | |
| 4 | 3-OMe | c-Bu | c-Hex | 7 | |
| 3 | 3-OMe | i-Pr | c-Hex | 2 | |
| 1 | 2-OMe | i-Pr | c-Hex | 38 | 2 |

What is claimed is:

1. A compound of the formula

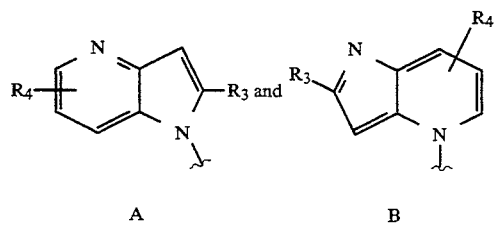

or a pharmaceutically acceptable salt thereof wherein HET is selected from the group consisting of A and B structures m is an integer from 1 to 4;

$R_1$ and $R_2$ are each independently selected from the group consisting of hydrogen; straight or branched alkyl of 1 to 15 carbon atoms, cycloalkyl having 3 to 8 carbon atoms optionally substituted by one or more alkyl group of 1 to 6 carbon atoms, bicycloalkyl having 3 to 8 carbon atoms in each ring, phenyl optionally substituted by one or more groups independently selected from the group consisting of alkyl having 1 to 6 carbon atoms and halogen, straight or branched alkenyl having 3 to 15 carbon atoms, cycloalkenyl having 5 to 8 carbon atoms;

$R_3$ is selected from hydrogen, alkyl, hydroxyalkyl, formyl, haloalkyl, cycloalkyl, alkylcycloalkyl, cycloalkylalkyl, cycloalkylhaloalkyl, aryloxyalkyl, alkoxyalkyl, alkylcarbonyl, alkylcarbonylalkyl, alkoxycarbonyl, alkenyl, cycloalkenyl, alkynyl, alkylcarbonyloxyalkyl, alkoxycarbonylalkyl, aralkoxycarbonylalkyl, aralkylcarbonyloxyalkyl, alkylsilyloxyalkyl, aryl/alkylsilyloxyalkyl, arylsilyloxyalkyl, mercaptoalkyl, alkylthioalkyl, alkylsulfinylalkyl, alkylsulfonylalkyl, and may further be an amino or amido radical of the formulae

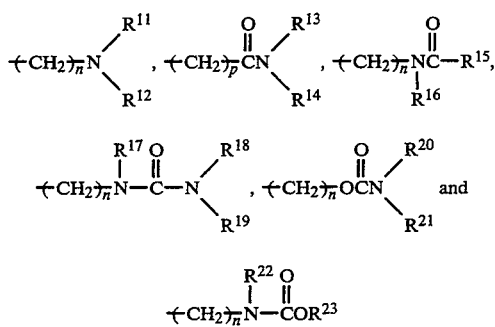

wherein n is an integer from one to six, inclusive; wherein p is an integer from zero to six; wherein each of $R^{11}$ through $R^{23}$ is independently selected from hydrogen, alkyl, cycloalkyl, hydroxyalkyl, cycloalkylalkyl, alkoxyalkyl, aralkyl and aryl;

X is selected from the group consisting of hydrogen, straight or branched alkyl of 1 to 6 carbon atoms, alkoxy of 1 to 6 carbon atoms, alkoxyalkyl, alkylthio wherein the alkyl has 1 to 6 carbon atoms, hydroxyalkyl wherein the alkyl has 1 to 6 carbon atoms, alkylthioalkyl wherein the alkyl groups are each 1 to 6 carbon atoms, cyano, hydroxy, amino, alkylamino wherein the alkyl groups have 1 to 6 carbon atoms, dialkylaminoalkyl, dialkylamino wherein the alkyl groups have 1 to 6 carbon atoms and halogen; and wherein $R_4$ is selected from the group consisting of alkyl of one to six carbon atoms, halogen, alkoxy of one to six carbon atoms and alkylthio.

2. A compound according to claim 1 wherein HET is A.

3. A compound according to claim 2 wherein $R_1$ is cycloalkyl and $R_2$ is cycloalkyl.

4. A compound according to claim 3 which is N-cyclohexyl-N-cyclopentyl-3-methyl-4-(1H-pyrrolo[3,2-b]pyridin-1-ylmethyl)benzamide.

5. A compound according to claim 3 which is N-cyclopentyl-N-(3,5-dimethylcyclohexyl)-2-methoxy-4-(1H-pyrrolo[3,2-b]pyridin-1-ylmethyl)benzamide.

6. A compound according to claim 3 which is N-cyclobutyl-N-cyclohexyl-2-methoxy-4-(1H-pyrrolo[3,2-b]pyridin-1-ylmethyl)benzamide.

7. A compound according to claim 2 wherein $R_1$ is alkyl and $R_2$ is cycloalkyl.

8. A compound according to claim 7 which is N-cyclohexyl-3-methoxy-N-(1-methylethyl)-4-(1H-pyrrolo[3,2-b]pyridin-1-ylmethyl)benzamide.

9. A compound according to claim 7 which is N-cyclohexyl-2-methoxy-N-(1-methylethyl)-4-(1H-pyrrolo[3,2-b]pyridin-1-ylmethyl)benzamide.

10. A compound according to claim 7 which is 3-bromo-N-cyclohexyl-N-(1-methylethyl)-4-(1H-pyrrolo[3,2-b]pyridin-1-ylmethyl)benzamide.

11. A compound according to claim 1 wherein HET is B.

12. A compound according to claim 11 wherein $R_1$ is alkyl and $R_2$ is cycloalkyl.

13. A compound according to claim 12 which is N-cyclohexyl-3-methoxy-N-(1-methylethyl)-4-(4H-pyrrolo[3,2-b]pyridin-4-ylmethyl) benzamide.

14. A pharmaceutical composition comprising a therapeutically effective amount of a compound of the formula

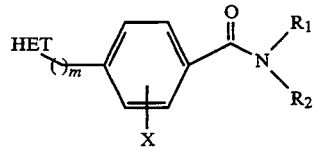

or a pharmaceutically acceptable salt thereof wherein HET is selected from the group consisting of

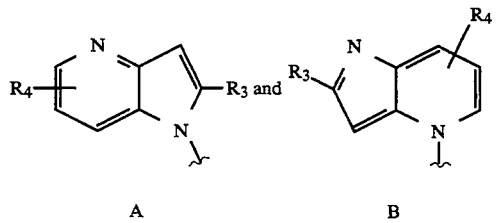

m is an integer from one to four;

$R_1$ and $R_2$ are each independently selected from the group consisting of hydrogen; straight or branched alkyl of 1 to 15 carbon atoms, cycloalkyl having 3 to 8 carbon atoms optionally substituted by one or more alkyl group of 1 to 6 carbon atoms, bicycloalkyl having 3 to 8 carbon atoms in each ring, phenyl optionally substituted by one or more groups independently selected from the group consisting of alkyl having 1 to 6 carbon atoms and halogen, straight or branched alkenyl having 3 to 15 carbon atoms, cycloalkenyl having 5 to 8 carbon atoms;

$R_3$ is selected from hydrogen, alkyl, hydroxyalkyl, formyl, halo, haloalkyl, cycloalkyl, alkylcycloalkyl, cycloalkylalkyl, cycloalkylhaloalkyl, cycloalkylcarbonyl, alkoxy, aralkyl, aralkylhaloalkyl, aryl, haloaryl, aroyl, aryloxyalkyl, alkoxyalkyl, alkylcarbonyl, alkylcarbonylalkyl, alkoxycarbonyl, alkenyl, cycloalkenyl, alkynyl, alkylcarbonyloxyalkyl, alkoxycarbonylalkyl, aralkoxycarbonylalkyl, aralkylcarbonyloxyalkyl, alkylsilyloxyalkyl, aryl/alkylsilyloxyalkyl, arylsilyloxyalkyl, mercaptoalkyl, alkylthioalkyl, alkylsulfinylalkyl, alkylsulfonylalkyl, and may further be an amino or amido radical of the formulae

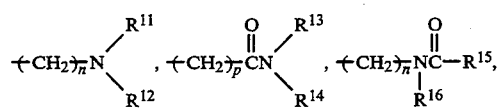

-continued

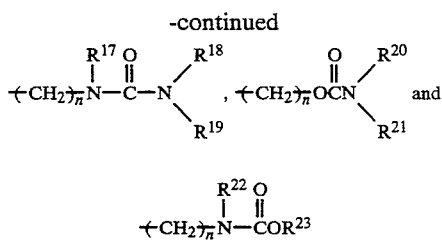

wherein n is an integer from one to six, inclusive; wherein p is an integer from zero to six; wherein each of $R^{11}$ through $R^{23}$ is independently selected from hydrogen, alkyl, cycloalkyl, hydroxyalkyl, cycloalkylalkyl, alkoxyalkyl, aralkyl and aryl;

X is selected from the group consisting of hydrogen, straight or branched alkyl of 1 to 6 carbon atoms, alkoxy of 1 to 6 carbon atoms, alkylthio wherein the alkyl has 1 to 6 carbon atoms, hydroxyalkyl wherein the alkyl has 1 to 6 carbon atoms, alkoxyalkyl, alkylthioalkyl wherein the alkyl groups are each 1 to 6 carbon atoms, cyano, hydroxy, amino, alkylamino wherein the alkyl groups have 1 to 6 carbon atoms, dialkylaminoalkyl, dialkylamino wherein the alkyl groups have 1 to 6 carbon atoms and halogen; and wherein $R_4$ is selected from the group consisting of alkyl of one to six carbon atoms, halogen, alkoxy of one to six carbon atoms and alkylthio.

15. A pharmaceutical composition according to claim 14 wherein the compound is selected from the group consisting of N-cyclohexyl-N-cyclopentyl-3-methyl-4-(1H-pyrrolo[3,2-b]pyridin-1-ylmethyl)benzamide;

N-cyclopentyl-N-(3,5-dimethylcyclohexyl)-2-methoxy-4-(1H-pyrrolo[3,2-b]pyridin-1-ylmethyl)-benzamide;

N-cyclobutyl-N-cyclohexyl-2-methoxy-4-(1H-pyrrolo[3,2-b]pyridin-1-ylmethyl) benzamide;

N-cyclohexyl-3-methoxy-N-(1-methylethyl)-4-(1H-pyrrolo[3,2-b]pyridin-1-ylmethyl)benzamide;

N-cyclohexyl-3-methoxy-N-(1-methylethyl)-4-(4H-pyrrolo[3,2-b]pyridin-4-ylmethyl) benzamide;

N-cyclohexyl-2-methoxy-N-(1-methylethyl)-4-(1H-pyrrolo[3,2-b]pyridin-1-ylmethyl)benzamide; and 3-bromo-N-cyclohexyl-N-(1-methylethyl)-4-(1H-pyrrolo[3,2-b]pyridin-1-ylmethyl)benzamide.

16. A method of treating diseases mediated by platelet activating factor comprising administering to a patient in need of treatment therapeutically effective amount of a compound of the formula

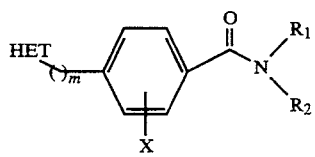

or a pharmaceutically acceptable salt thereof wherein Het is selected from the group consisting of

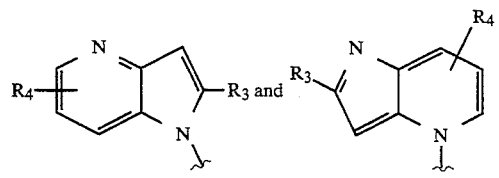

m is an integer from 1 to 4;

$R_1$ and $R_2$ are each independently selected from the group consisting of hydrogen; straight or branched alkyl of 1 to 15 carbon atoms, cycloalkyl having 3 to 8 carbon atoms optionally substituted by one or more alkyl group of 1 to 6 carbon atoms, bicycloalkyl having 3 to 8 carbon atoms in each ring, phenyl optionally substituted by one or more groups independently selected from the group consisting of alkyl having 1 to 6 carbon atoms and halogen, straight or branched alkenyl having 3 to 15 carbon atoms, cycloalkenyl having 5 to 8 carbon atoms;

$R_3$ is selected from hydrogen, alkyl, hydroxyalkyl, formyl, haloalkyl, cycloalkyl, alkylcycloalkyl, cycloalkylalkyl, cycloalkylhaloalkyl, cycloalkylcarbonyl, aralkyl, aralkylhaloalkyl, aryl, haloaryl, aroyl, aryloxyalkyl, alkoxyalkyl, alkylcarbonyl, alkylcarbonylalkyl, alkoxycarbonyl, alkenyl, cycloalkenyl, alkynyl, carboxyl, carboxyalkyl, alkylcarbonyloxyalkyl, alkoxycarbonylalkyl, aralkoxycarbonylalkyl, aralkylcarbonyloxyalkyl, alkylsilyloxyalkyl, aryl/alkylsilyloxyalkyl, arylsilyloxyalkyl, mercaptoalkyl, alkylsulfinylalkyl, alkylsulfonylalkyl, and may further be an amino or amido radical of the formulae

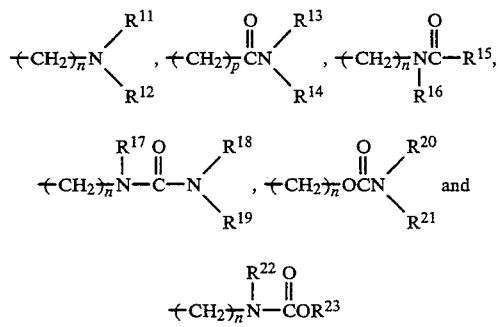

wherein n is an integer from one to six, inclusive; wherein p is an integer from zero to six; wherein each of $R^{11}$ through $R^{23}$ is independently selected from hydrogen, alkyl, cycloalkyl, hydroxyalkyl, cycloalkylalkyl, alkoxyalkyl, aralkyl and aryl;

X is selected from the group consisting of hydrogen, straight or branched alkyl of 1 to 6 carbon atoms, alkoxy of 1 to 6 carbon atoms, alkylthio wherein the alkyl has 1 to 6 carbon atoms, hydroxyalkyl wherein the alkyl has 1 to 6 carbon atoms, alkoxyalkyl, alkylthioalkyl wherein the alkyl groups are each 1 to 6 carbon atoms, cyano, hydroxy, amino, alkylamino wherein the alkyl groups have 1 to 6 carbon atoms, dialkylaminoalkyl, dialkylamino wherein the alkyl groups have 1 to 6 carbon atoms and halogen; and wherein R₄ is selected from the group consisting of alkyl of one to six carbon atoms, halogen, alkoxy of one to six carbon atoms and alkylthio.

17. A method according to claim 16 wherein the compound is selected from the group consisting of N-cyclohexyl-N-cyclopentyl-3-methyl-4-(1H-pyrrolo[3,2-b]pyridin-1-ylmethyl)benzamide;

N-cyclohexyl-3-methoxy-N-(1-methylethyl)-4-(4H-pyrrolo[3,2-b]pyridin-4-ylmethyl)benzamide;

N-cyclopentyl-N-(3,5-dimethylcyclohexyl)-2-methoxy-4-(1H-pyrrolo[3,2-b]pyridin-1-ylmethyl)-benzamide; and N-cyclobutyl-N-cyclohexyl-2-methoxy-4-(1H-pyrrolo[3,2-b]pyridin-1-ylmethyl)benzamide.

N-cyclohexyl-3-methoxy-N-(1-methylethyl)-4-(1H-pyrrolo[3,2-b]pyridin-1-ylmethyl)benzamide;

N-cyclohexyl-2-methoxy-N-(1-methylethyl)-4-(1H-pyrrolo[3,2-b]pyridin-1-ylmethyl)benzamide; and 3-bromo-N-cyclohexyl-N-(1-methylethyl)-4-(1H-pyrrolo[3,2-b]pyridin-1-ylmethyl)benzamide.

18. A method according to claim 17 wherein the disease is asthma.

19. A method according to claim 17 wherein the disease is septic shock.

* * * * *

UNITED STATES PATENT AND TRADEMARK OFFICE
CERTIFICATE OF CORRECTION

PATENT NO. : 5,360,907
DATED : November 1, 1994
INVENTOR(S) : Lentz, et al.

It is certified that error appears in the above-indentified patent and that said Letters Patent is hereby corrected as shown below:

Column 9, lines 30-35 that part of the structure reading

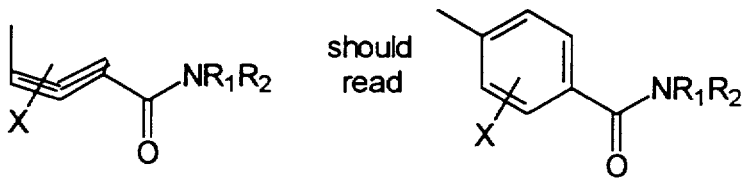

Column 24, line 42, reading "Chem., 2," should read -- Chem., 6, --.

Signed and Sealed this

Twelfth Day of December, 1995

Attest:

BRUCE LEHMAN

Attesting Officer

Commissioner of Patents and Trademarks